US011545238B2

United States Patent
Greving et al.

(10) Patent No.: US 11,545,238 B2
(45) Date of Patent: Jan. 3, 2023

(54) MACHINE LEARNING METHOD FOR PROTEIN MODELLING TO DESIGN ENGINEERED PEPTIDES

(71) Applicant: iBio, Inc., Bryan, TX (US)

(72) Inventors: Matthew P. Greving, San Carlos, CA (US); Alexander T. Taguchi, San Carlos, CA (US); Kevin E. Hauser, San Carlos, CA (US)

(73) Assignee: IBIO, INC., Bryan, TX (US)

( * ) Notice: Subject to any disclaimer, the term of this patent is extended or adjusted under 35 U.S.C. 154(b) by 0 days.

(21) Appl. No.: 17/108,958

(22) Filed: Dec. 1, 2020

(65) Prior Publication Data

US 2021/0166788 A1 Jun. 3, 2021

Related U.S. Application Data

(63) Continuation of application No. PCT/US2020/032724, filed on May 13, 2020.

(60) Provisional application No. 62/855,767, filed on May 31, 2019.

(51) Int. Cl.
| | | |
|---|---|---|
| G16B 40/20 | (2019.01) | |
| G06N 20/00 | (2019.01) | |
| G16B 5/30 | (2019.01) | |
| G06N 5/04 | (2006.01) | |
| G16B 5/00 | (2019.01) | |
| C07K 14/00 | (2006.01) | |

(52) U.S. Cl.
CPC ............ *G16B 40/20* (2019.02); *C07K 14/001* (2013.01); *G06N 5/04* (2013.01); *G06N 20/00* (2019.01); *G16B 5/00* (2019.02); *G16B 5/30* (2019.02)

(58) Field of Classification Search
None
See application file for complete search history.

(56) References Cited

U.S. PATENT DOCUMENTS

| | | |
|---|---|---|
| 7,894,995 B2 | 2/2011 | Jojic et al. |
| 8,050,870 B2 | 11/2011 | Heckerman et al. |
| 8,374,828 B1 | 2/2013 | Jacobs et al. |
| 10,431,325 B2 | 10/2019 | Agrawal et al. |
| 2006/0020396 A1 | 1/2006 | Gantier et al. |
| 2007/0016380 A1 | 1/2007 | Smythe et al. |
| 2018/0009850 A1 | 1/2018 | Raman et al. |
| 2018/0068054 A1 | 3/2018 | Saker et al. |
| 2019/0065677 A1 | 2/2019 | Gifford et al. |
| 2020/0279616 A1 | 9/2020 | Rooney et al. |

FOREIGN PATENT DOCUMENTS

| | | |
|---|---|---|
| EP | 1 510 959 A2 | 3/2005 |
| EP | 3 417 874 A1 | 12/2018 |
| KR | 10-2018-0012747 A | 2/2018 |
| WO | WO-2002/064734 A2 | 8/2002 |
| WO | WO-2016/005969 A1 | 8/2002 |
| WO | WO-2016/164305 A1 | 10/2016 |
| WO | WO-2018/201020 A1 | 11/2018 |
| WO | 2020102603 A1 | 5/2020 |

OTHER PUBLICATIONS

Zhou, P., et al. "Computational peptidology: a new and promising approach to therapeutic peptide design." Current Medicinal Chemistry 20.15 (2013): 1985-1996.*
Correia, B.E. et al. (2010). "Computational design of epitope-scaffolds allows induction of antibodies specific for a poorly immunogenic HIV vaccine epitope," Structure 18:1116-1126.
Das, R. et al. (2008). "Macromolecular modeling with rosetta," Annu. Rev. Biochem. 77:363-382.
International Search Report dated Sep. 25, 2020, for PCT Application No. PCT/US2020/032724, filed on May 13, 2020, 4 pages.
Ofek, G. et al. (2010). "Elicitation of structure-specific antibodies by epitope scaffolds," PNAS 107:17880-17887.
Written Opinion of the International Searching Authority dated Sep. 25, 2020, for PCT Application No. PCT/US2020/032724, filed on May 13, 2020, 8 pages.
Elton, D.C., et al., "Deep learning for molecular design—a review of the state of the art," Mol. Syst. Des. Eng., 2019, 828-849, vol. 4.
Bengio, Y., et al., "Representation Learning: A Review and New Perspectives," IEEE Transactions on Pattern Analysis and Machine Intelligence, Mar. 7, 2013, pp. 1798-1828, vol. 35, Issue 8.
Jumper, J., et al., Highly accurate protein structure prediction with AlphaFold, Nature, Aug. 26, 2021, pp. 583-589, vol. 596, No. 7873.
Gao, W., et al., Deep Learning in Protein Structural Modeling and Design, Patterns, Dec. 11, 2020, 23 pages, pp. vol. 1, Issue 9.
Ofek, et al., Elicitation of structure-specific antibodies by epitope scaffolds, PNAS, 2010, pp. 17880-17887, vol. 107.
United States Patent Trademark Office (ISA), International Search Report and Written Opinion for PCT/US2020/032715 dated Nov. 16, 2021, 9 pp.
Sinha et al., "Dissecting the Non-specific and Specific Components of the Initial Folding Reaction of Barstar by Multisite FRET Measurements," J. Mol. Biol. (2007) 370, 385-405 (21 pages).
United States Patent Trademark Office (ISA), International Search Report and Written Opinion for PCT/US2021/61289 dated Feb. 23, 2022, 12 pp.

* cited by examiner

*Primary Examiner* — G Steven Vanni
(74) *Attorney, Agent, or Firm* — Edwin S. Flores; Daniel J. Chalker; Chalker Flores, LLP

(57) ABSTRACT

Provided herein are methods for design of engineered polypeptides that recapitulate molecular structure features of a predetermined portion of a reference protein structure, e.g., an antibody epitope or a protein binding site. A Machine Learning (ML) model is trained by labeling blueprint records generated from a reference target structure with scores calculated based on computational protein modeling of polypeptide structures generated by the blueprint records. The method may include training an ML model based on a first set of blueprint records, or representations thereof, and a first set of scores, each blueprint record from the first set of blueprint records associated with each score from the first set of scores. After the training, the machine learning model may be executed to generate a second set of blueprint records. A set of engineered polypeptides are then generated based on the second set of blueprint records.

18 Claims, 16 Drawing Sheets

300 receiving a reference target structure for a reference target 301

↓ generating the first set of blueprint records from a predetermined portion of the reference target structure, each blueprint record from the first set of blueprint records includes target residue positions and scaffold residue positions, each target residue position corresponding to one target residue from the set of target residues 302

↓ training a machine learning model based on a first set of blueprint records, or representations thereof, and a first set of scores, each blueprint record from the first set of blueprint records associated with each score from the first set of scores 303

↓ executing, after the training, the machine learning model to generate a second set of blueprint records having at least one desired score 304

↓ determining whether to retrain the machine learning model by calculating a second set of scores for the second set of blueprint records 305

↓ retraining, in response to the determining, the machine learning model based on (1) retraining blueprint records that include the second set of blueprint records and (2) retraining scores that include the second set of scores 306

FIG. 3

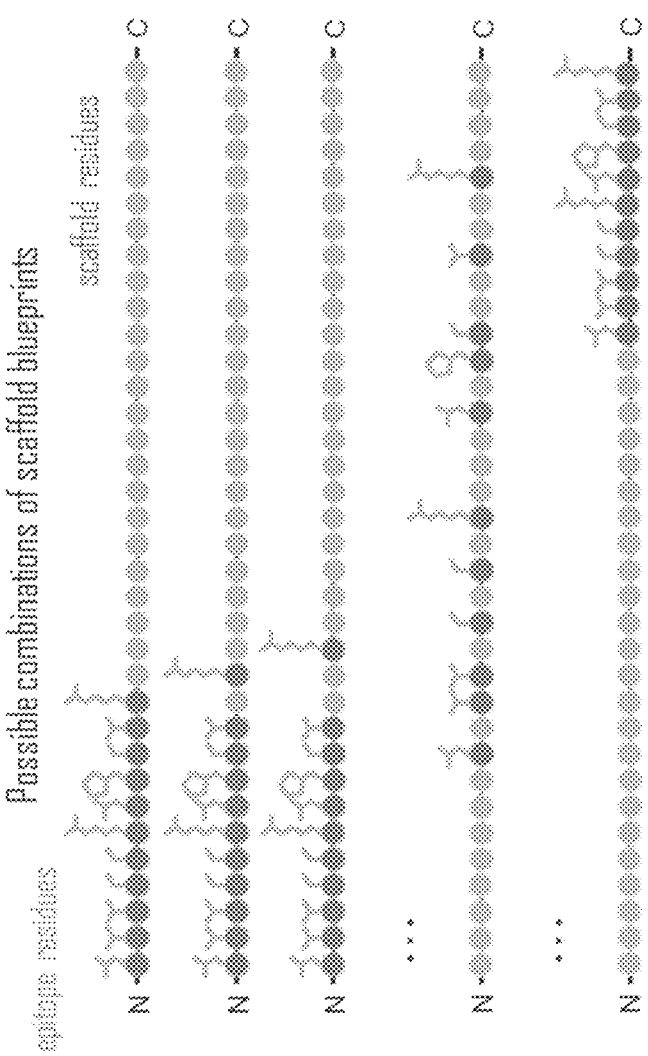
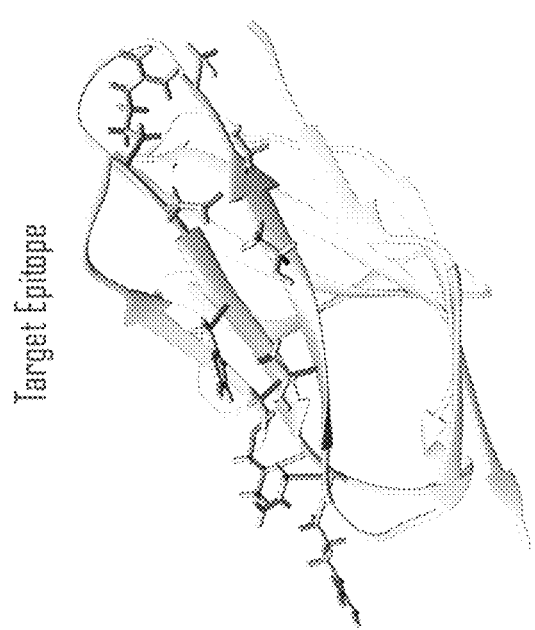
FIG. 5

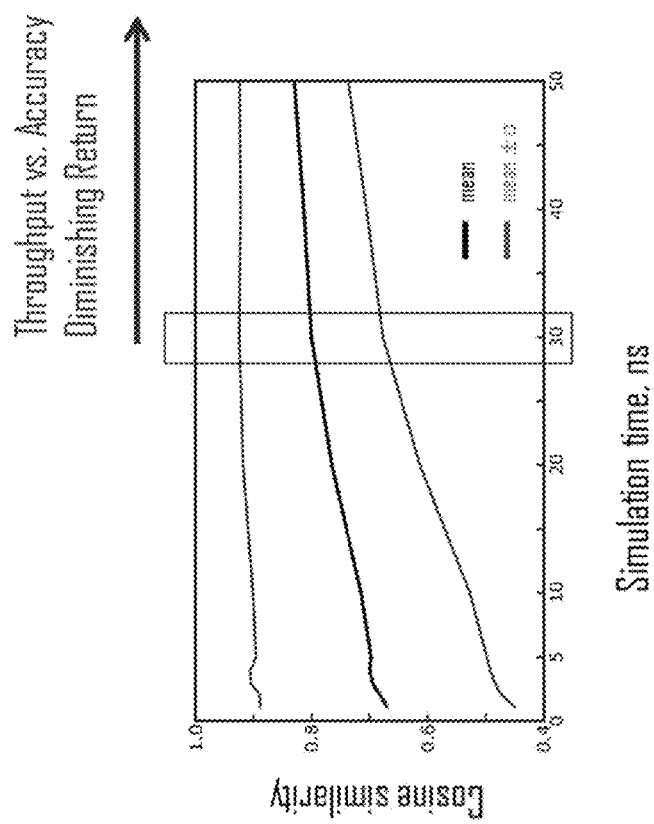
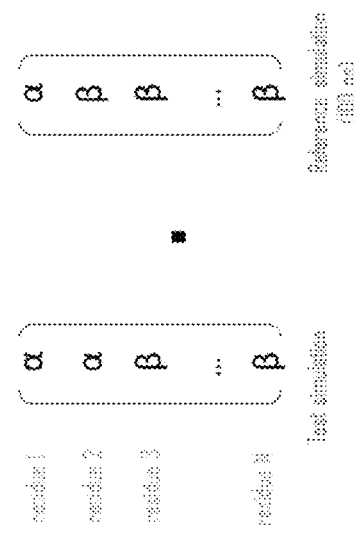
FIG. 11

MACHINE LEARNING METHOD FOR PROTEIN MODELLING TO DESIGN ENGINEERED PEPTIDES

CROSS REFERENCE TO RELATED APPLICATION

This application is a continuation of International Patent Application No. PCT/US2020/032724, filed May 13, 2020, which claims priority to and the benefit of U.S. Provisional Patent Application No. 62/855,767, filed May 31, 2019 and titled "Meso-Scale Engineered Peptides and Methods of Selecting," which is incorporated herein by reference in its entirety.

TECHNICAL FIELD

The present disclosure generally relates to the field of artificial intelligence/machine learning, and in particular to methods and apparatus for training and using a machine learning model for engineering peptides.

BACKGROUND

Computational design can be used in the design of new therapeutic proteins that mimic native proteins or to design vaccines that display a desired epitope or epitopes from a pathogenic antigen. Computationally designed proteins may also be used to generate or select for binding agents. For example, one can pan libraries of antibodies (e.g. phage display libraries) against a designed protein bait to select for clones that bind to that bait, or one can immunize experimental animals with a designed immunogen to generate novel antibodies.

Although there are others, the leading modeling platform for computational design is Rosetta (Das and Baker, 2008). This platform can be used for design of proteins that match a desired structure. Correia et al., *Structure* 18:1116-26 (2010) discloses a general computational method to design epitope-scaffolds in which contiguous structural epitopes are transplanted into scaffold proteins for conformational stabilization and immune presentation. Olek et al., *PNAS USA* 107:17880-87 (2010) discloses transplantation of an epitope from the HIV-1 gp41 protein into select acceptor scaffolds.

Conventional computational design techniques typically rely upon grafting a portion of a target protein structure (e.g., an epitope) onto a pre-existing scaffold. Modeling platforms such as Rosetta are too computationally intensive to adequately explore large topology spaces, such as the vast topology space of proteins that recapitulate a given protein structure. Thus, there is a need for new and improved devices and methods for computational design of proteins that mimic a target protein structure.

SUMMARY

Generally, in some variations, an apparatus may include a non-transitory processor-readable medium that stores code representing instructions to be executed by a processor. The code may comprise code to cause the processor to train a machine learning model based on a first set of blueprint records, or representations thereof, and a first set of scores, each blueprint record from the first set of blueprint records associated with each score from the first set of scores. The medium may include code to execute, after the training, the machine learning model to generate a second set of blueprint records having at least one desired score. The second set of blueprint records may be configured to be received as input in computational protein modeling to generate engineered polypeptides based on the second set of blueprint records.

The medium may include code to cause the processor to receive a reference target structure. The medium may include code to cause the processor to generate the first set of blueprint records from a predetermined portion of the reference target structure, each blueprint record from the first set of blueprint records comprising target residue positions and scaffold residue positions, each target residue position from the set of target residue positions corresponding to one target residue from the set of target residues. In some variations, in at least one blueprint record, the target residue positions are nonconsecutive. In some variations, in at least one blueprint record, target residue positions are in an order different from the order of the target residues positions in the reference target sequence.

The medium may include code to cause the processor to label the first set of blueprint records by performing computational protein modeling on each blueprint record to generate a polypeptide structure, calculating a score for the polypeptide structure, and associating the score with the blueprint record. In some variations, the computational protein modeling may be based on a de novo design without template matching to the reference target structure. In some variations, each score comprises an energy term and a structure-constraint matching term that may be determined using one or more structural constraints extracted from the representation of the reference target structure.

The medium may include code to cause the processor to determine whether to retrain the machine learning model by calculating a second set of scores for the second set of blueprint records. The medium may include further code to retrain, in response to the determining, the machine learning model based on (1) retraining blueprint records that include the second set of blueprint records and (2) retraining scores that include the second set of scores.

The medium may include code to cause the processor to concatenate, after the retraining of the machine learning model, the first set of blueprint records and the second set of blueprint records to generate the retraining of blueprint records and to generate the retraining scores, each blueprint record from the retraining of blueprint records associated with a score from the retraining scores. In some variations, at least one desired score may be a preset value. In some variations, the at least one desired score may be dynamically determined.

In some variations, the machine learning model may be a supervised machine learning model. The supervised machine learning model may include an ensemble of decision trees, a boosted decision tree algorithm, an extreme gradient boosting (XGBoost) model, or a random forest. In some variations, the supervised machine learning model may include a support vector machine (SVM), a feed-forward machine learning model, a recurrent neural network (RNN), a convolutional neural network (CNN), graph neural network (GNN), or a transformer neural network.

In some variations, the machine learning model may include an inductive machine learning model. In some variations, the machine learning model may include a generative machine learning model.

The medium may include code to cause the processor to perform computational protein modeling on the second set of blueprint records to generate engineered polypeptides.

The medium may include code to cause the processor to filter the engineered polypeptides by static structure comparison to the representation of the reference target structure.

The medium may include code to cause the processor to filter the engineered polypeptides by dynamic structure comparison to the representation of the reference target structure using molecular dynamics (MD) simulations of the representation of the reference target structure and each of the engineered polypeptides. In some variations, MD simulations are performed in parallel using symmetric multiprocessing (SMP).

BRIEF DESCRIPTION OF THE DRAWINGS

FIG. 3 is a schematic description of an exemplary method of engineered polypeptide design.

FIG. 5 is a schematic description of an exemplary method of preparing data for an engineered polypeptide design device.

FIG. 11 illustrates exemplary methods of performing molecular dynamics simulations to verify engineered polypeptides.

DETAILED DESCRIPTION

Figure 1:
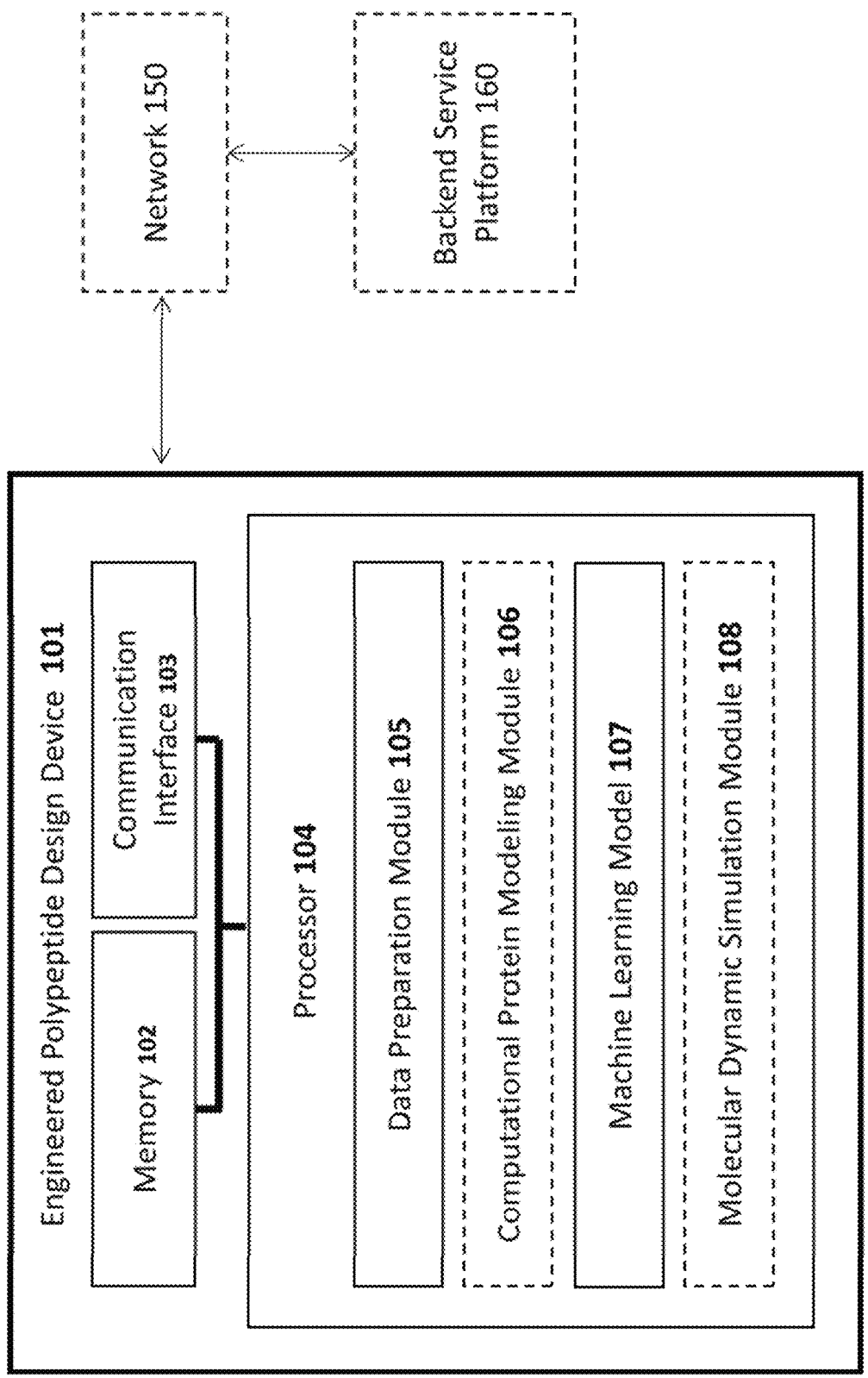
FIG. 1 is a schematic description of an exemplary engineered polypeptide design device.

Non-limiting examples of various aspects and variations of the invention are described herein and illustrated in the accompanying drawings.

Provided herein are methods of designing engineered polypeptides, and compositions comprising and methods of using said engineered peptides. For example, provided herein are methods of using engineered peptides in in vitro selection of antibodies. In some aspects, a user (or program) may select a target protein having a known structure and identify a portion of the target protein as input for design of an engineered polypeptide. The target protein may be an antigen (or putative antigen) from a pathogenic organism; a protein involved in cellular functions associated with disease; an enzyme; a signaling molecule; or any protein for which an engineered polypeptide recapitulating a portion of the protein is desired. The engineered polypeptide may be intended for antibody discovery, vaccination, diagnostic, use in a method of treatment, biomanufacturing, or other applications. The "target protein" may, in a variation, be more than one protein, such as a multimeric protein complex. For simplicity, the disclosure refers to a target protein, but the methods apply to multimeric structures as well. In a variation, the target protein is two or more distinct proteins or protein complexes. For example, the methods disclosed herein may be used to design engineered peptides that mimic common attributes of proteins from diverse species—e.g., to target a conserved epitope for antibody selection.

A computational record of the topology of the protein is derived, termed here a "reference target structure." The reference target structure may be a conventional protein structure or a structural model, represented for example by 3D coordinates for all (or most) atoms in the protein or 3D coordinates for select atoms (e.g., coordinates of the CP atoms of each protein residue). Optionally the reference target structure may include dynamic terms derived either computationally (e.g., from molecular dynamics simulation) or experimentally (e.g., from spectroscopy, crystallography, or electron microscopy).

The predetermined portion of the target protein is converted into a blueprint having target-residue positions and scaffold-residue positions. Each position may be assigned either a fixed amino-acid residue identity or a variable identity (e.g., any amino acid, or an amino acid with desired physiochemical properties—polar/non-polar, hydrophobicity, size, etc.). In a variation, each amino acid from the predetermined portion of the target protein is mapped to one target-residue position, which is assigned to have the same amino-acid identity as found in the target protein. The target-residue positions may be continuous and/or ordered. An advantage, however, in some variations, is that the target-residue position may be discontinuous (interrupted by scaffold-residue positions) and not ordered (in a different order from the target protein). Unlike grafting approaches, in some variations, the order of residues is not constrained. Similarly, the disclosed methods can accommodate discontinuous portions of the target protein (e.g., discontinuous epitopes where different portions of the same protein or even different protein chains contribute to one epitope).

The scaffold-residue positions of the blueprint may be assigned to have any amino acid at that position (i.e., an X representing any amino acid). In variations, the scaffold-residue position is assigned by selection from a subset of possible natural or unnatural amino acids (e.g., small polar amino acid residue, large hydrophobic amino-acid residue, etc.). The blueprint may also accommodate optional target- and/or scaffold-residue positions. Similarly stated, the blueprint may tolerate insertion or deletion of residue positions. For example, a target- or scaffold-residue position may be assigned to be present or absent; or the position may be assigned to be 0, 1, 2, 3, 4, 5, 6, 7, 8, 9, 10, or more residues.

A subset of the blueprints may then be used to perform computational modeling to generate corresponding polypeptide structures, using, e.g., energy terms(s) and topological constraint(s) derived from the reference target structure, with a score calculated for each polypeptide structure. A machine learning (ML) model may be trained using the scores and the blueprints, or representations of the blueprints (e.g., vectors that represent the blueprints), and the ML model may be executed to generate further blueprints. An advantage of this method is that the topological space covered by vastly more blueprints may be explored by the ML model than could be explored by iterative computational modeling of many blueprints.

The disclosure further provides methods and related devices to convert output blueprints to sequences and/or structures of engineered polypeptides, and to compare these engineered polypeptides to the target protein—using static comparison, dynamic comparison or both—and to filter the polypeptides using these comparisons.

While the methods and apparatus are described herein as processing data from a set of blueprint records, a set of scores, a set of energy terms, a set of molecular dynamics energies, a set of energy terms, or a set of energy functions, in some instances an engineered polypeptide design device 101 as shown and described with respect FIG. 1, may be used to generate the set blueprint records, the set of scores, the set of energy terms, the set of molecular dynamics energies, the set of energy terms, or the set of energy functions. Therefore, the engineered polypeptide design device 101 may be used to generate or process any collection or stream of data, events, and/or objects. For example, the engineered polypeptide design device 101 may process and/or generate any string(s), number(s), name(s), image(s), video(s), executable file(s), dataset(s), spreadsheet(s), data file(s), blueprint file(s), and/or the like. For further examples, the engineered polypeptide design device 101 may process and/or generate any software code(s), webpage(s), data file(s), model file(s), source file(s), script(s), and/or the like. As another example, the engineered polypeptide design device 101 may process and/or generate data stream(s), image data stream(s), textual data stream(s), numerical data stream(s), computer aided design (CAD) file stream(s), and/or the like.

FIG. 1 is a schematic description of an exemplary engineered polypeptide design device 101. The engineered polypeptide design device may be used to generate a set of engineered polypeptide designs. The engineered polypeptide design device 101 includes a memory 102, a communication interface 103, and a processor 104. The engineered polypeptide design device 101 can be optionally connected (without intervening components) or coupled (with or without intervening components) to a backend service platform 160, via a network 150. The engineered polypeptide design device 101 can be a hardware-based computing device, such as, for example, a desktop computer, a server computer, a mainframe computer, a quantum computing device, a parallel computing device, a desktop computer, a laptop computer, an ensemble of smartphone devices, and/or the like.

The memory 102 of the engineered polypeptide design device 101 may include, for example, a memory buffer, a random access memory (RAM), a read-only memory (ROM), an erasable programmable read-only memory (EPROM), an embedded multi-time programmable (MTP) memory, an embedded multi-media card (eMMC), a universal flash storage (UFS) device, and/or the like. The memory 102 may store, for example, one or more software modules and/or code that includes instructions to cause the processor 104 of the engineered polypeptide design device 101 to perform one or more processes or functions (e.g., a data preparation module 105, a computational protein modeling module 106, a machine learning model 107, and/or a molecular dynamics simulation module 108). The memory 102 may store a set of files associated with (e.g., generated by executing) the machine learning model 107 including data generated by the machine learning model 107 during the operation of the engineered polypeptide design device 101. In some instances, the set of files associated with the machine learning model 107 may include temporary variables, return memory addresses, variables, a graph of the machine learning model 107 (e.g., a set of arithmetic operations or a representation of the set of arithmetic operations used by the machine learning model 107), the graph's metadata, assets (e.g., external files), electronic signatures (e.g., specifying a type of the machine learning model 107 being exported, and the input/output tensors), and/or the like, generated during the operation of the engineered polypeptide design device 101.

The communication interface 103 of the engineered polypeptide design device 101 can be a hardware component of the engineered polypeptide design device 101 operatively coupled to and used by the processor 104 and/or the memory 102. The communication interface 103 may include, for example, a network interface card (NIC), a Wi-Fi™ module, a Bluetooth® module, an optical communication module, and/or any other suitable wired and/or wireless communication interface. The communication interface 103 may be configured to connect the engineered polypeptide design device 101 to the network 150, as described in further detail herein. In some instances, the communication interface 103 may facilitate receiving or transmitting data via the network 150. More specifically, in some implementations, the communication interface 103 may facilitate receiving or transmitting data such as, for example, a set of blueprint records, a set of scores, a set of energy terms, a set of molecular dynamics energies, a set of energy terms, or a set of energy functions through the network 150 from or to the backend service platform 160. In some instances, data received via communication interface 103 may be processed by the processor 104 or stored in the memory 102, as described in further detail herein.

The processor 104 may include, for example, a hardware based integrated circuit (IC) or any other suitable processing device configured to run and/or execute a set of instructions or code. For example, the processor 104 may be a general purpose processor, a central processing unit (CPU), a graphical processing unit (GPU), a tensor processing unit (TPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 104 is operatively coupled to the memory 102 through a system bus (for example, address bus, data bus and/or control bus).

The processor 104 may include a data preparation module 105, a computational protein modeling module 106, and a machine learning model 107. The processor 104 may optionally include a molecular dynamics simulation module 108. Each of the data preparation module 105, the computational protein modeling module 106, the machine learning model 107, or the molecular dynamics simulation module 108 can be software stored in memory 102 and executed by the processor 104. For example, a code to cause the machine learning model 107 to generate a set of blueprint records can be stored in the memory 102 and executed by the processor 104. Similarly, each of the data preparation module 105, the computational protein modeling module 106, the machine learning model 107, or the molecular dynamics simulation module 108 can be a hardware-based device. For example, a process to cause the machine learning model 107 to generate the set of blueprint records may be implemented on an individual integrated circuit (IC) chip.

The data preparation module 105 can be configured to receive (e.g., from the memory 102 or the backend service platform 160) a set of data including receiving a reference target structure for a reference target. The data preparation module 105 can be further configured to generate a set of blueprint records (e.g., a blueprint file encoded in a table of alphanumeric data) from a predetermined portion of the reference target structure. In some instances, each blueprint record from the set of blueprint records may include target residue positions and scaffold residue positions, each target residue position corresponding to one target residue from the set of target residues.

In some instances, the data preparation module 105 may be further configured to encode a blueprint of a reference target structure into a blueprint record. The data preparation module 105 may further convert the blueprint record into a representation of the blueprint record that is generally suitable for use in a machine learning model. In some instances, the representation may be a one-dimensional vector of numbers, a two-dimensional matrix of alphanumerical data, a three-dimensional tensor of normalized numbers. More specifically, in some instances, the representation is a vector of an ordered list of numbers of intervening scaffold residue positions. Such representation may be used because the order of the target-residues can be inferred from the target structure, therefore the representation does not need to identify the amino acid identity of the target-residue positions. One example of such representation is described further with respect to FIG. 6.

In some instances, the data preparation module 105 may generate and/or process a set blueprint records, a set of scores, a set of energy terms, a set of molecular dynamics energies, a set of energy terms, and/or a set of energy functions. The data preparation module 105 can be configured to extract information from the set of blueprint records, the set of scores, the set of energy terms, the set of molecular dynamics energies, the set of energy terms, or the set of energy functions.

In some instances, the data preparation module 105 may convert an encoding of the set of blueprint records to have a common character encoding such as for example, ASCII, UTF-8, UTF-16, Guobiao, Big5, Unicode, or any other suitable character encoding. In yet some other instances, the data preparation module 105 may be further configured to extract features of the blueprint record and/or the representation of the blueprint record by, for example, identifying a portion of the blueprint record or the representation of the blueprint record significant for engineering polypeptides. In some instances, the data preparation module 105 may convert the units of the set of blueprint records, the set of scores, the set of energy terms, the set of molecular dynamics energies, the set of energy terms, or the set of energy functions from the English unit such as, for example, mile, foot, inch, and/or the like, to the International System of units (SI) such as, for example, kilometer, meter, centimeter, and/or the like.

The computational protein modeling module 106 can be configured to generate a set of initial candidates of blueprint records that may serve as starting templates for computational optimization process described herein from a predetermined portion of the reference target structure. In one example, the computational protein modeling module 106 can be a Rosetta remodeler. Variations of the method employ other modeling algorithms, including without limitation molecular dynamics simulations, ab initio fragment assembly, Monte Carlo fragment assembly, machine learning structure prediction such as AlphaFold or trRosetta, structural knowledgebase-backed protein folding, neural network protein folding, sequence-based recurrent or transformer network protein folding, generative adversarial network protein structure generation, Markov Chain Monte Carlo protein folding, and/or the like. The initial candidate structures generated using Rosetta remodeler may be used as a training set for the machine learning model 107. The computational protein modeling module 106 can further computationally determine an energy term for each blueprint from the initial candidates of blueprint records. The data preparation module 105 can then be configured to generate a score from the energy term. In one example, the score can be a normalized value of the energy term. The normalized value can be a number from 0 to 1, a number from −1 to −1, a normalized value between 0 and 100, or any other numerical range. In some variations, the computational protein modeling module 106 may be based on a de novo design without template matching to the reference target structure or based on weak distance restraints where, for example, the distances between target residues are constrained to be within 1 angstrom of the target-residue distances in the target structure. Weak distance restraints may include restraints that allow variational noise distribution around distance restraints (e.g., a Gaussian noise with a specific mean and a specific variance around the distance restraints.) In some variations, the computational protein modeling module 106 may be used by smoothing or adding variational noise to any distance constraints and/or defining an objective function of a computational protein model such that the computational protein model is penalized less harshly when distant constraints are not met. Moreover, in some instances the computational protein modeling module 106 may use smooth labeling of the energy term. An advantage of this method is that by smoothing the energy term label the machine learning model 107 can more easily optimize the topological space covered by the blueprints to be explored.

The machine learning model 107 may be used to generate an improved blueprint record compared to the set of initial candidates of blueprint records. The machine learning model 107 can be a supervised machine learning model configured to receive the set of initial candidates of blueprint records and a set of scores, computed by the computational protein modeling module 106. Each score from the set of scores correspond to a blueprint records from the set of initial candidates of blueprint records. The processor 104 can be configured to associate each corresponding score and blueprint record to generate a set of labeled training data.

In some instances, the machine learning model 107 may include an inductive machine learning model and/or a generative machine learning model. The machine learning model may include a boosted decision tree algorithm, an ensemble of decision trees, an extreme gradient boosting (XGBoost) model, a random forest, a support vector machine (SVM), a feed-forward machine learning model, a recurrent neural network (RNN), a convolutional neural network (CNN), a graph neural network (GNN), an adversarial network model, an instance-based training model, a transformer neural network, and/or the like. The machine learning model 107 can be configured to include a set of model parameters including a set of weights, a set of biases, and/or a set of activation functions that, once trained, may be executed in an inductive mode to generate a score from a blueprint record or may be executed in a generative mode to generate a blueprint record from a score.

In one example, the machine learning model 107 can be a deep learning model that includes an input layer, an output layer, and multiple hidden layers (e.g., 5 layers, 10 layers, 20 layers, 50 layers, 100 layers, 200 layers, etc.). The multiple hidden layers may include normalization layers, fully connected layers, activation layers, convolutional layers, recurrent layers, and/or any other layers that are suitable for representing a correlation between the set of blueprint records and the set of scores, each score representing an energy term.

In one example, the machine learning model 107 can be an XGBoost model that includes a set of hyper-parameters such as, for example, a number of boost rounds that defines the number of boosting rounds or trees in the XGBoost model, maximum depth that defines a maximum number of permitted nodes from a root of a tree of the XGBoost model to a leaf of the tree, and/or the like. The XGBoost model may include a set of trees, a set of nodes, a set of weights, a set of biases, and other parameters useful for describing the XGBoost model.

In some implementations, the machine learning model 107 (e.g., a deep learning model, an XGBoost model, and/or the like) can be configured to iteratively receive each blueprint record from the set of blueprint records and generate an output. Each blueprint record from the set of blueprint records is associated with one score from the set of scores. The output and the score can be compared using an objective function (also referred to as 'cost function') to generate a first training loss value. The objective function may include, for example, a mean square error, a mean absolute error, a mean absolute percentage error, a logcosh, a categorical crossentropy, and/or the like. The set of model parameters can be modified in multiple iterations and the first objective function can be executed at each iteration until the first training loss value converges to a first predetermined training threshold (e.g. 80%, 85%, 90%, 97%, etc.).

In some implementations, the machine learning model 107 can be configured to iteratively receive each score from the set of scores and generate an output. Each blueprint record from the set of blueprint records is associated with one score from the set of scores. The output and the blueprint record can be compared using the objective function to generate a second training loss value. The set of model parameters can be modified in multiple iterations and the first objective function can be executed at each iteration of the multiple iterations until the second training loss value converges to a second predetermined training threshold.

Once trained, the machine learning model 107 may be executed to generate a set of improved blueprint records. The set of improved blueprint records may be expected to have higher scores than the set of initial candidates of blueprint records. In some instances, the machine learning model 107 may be a generative machine learning model that is trained on a first set of blueprint records (e.g., generated using Rosetta remodeler) corresponding to a first set of scores (e.g., each score having an energy term corresponding to Rosetta energy of a blueprint record from the set of blueprint records) to represent a correlation of the design space of the first set of blueprint records with the first set of scores (e.g., corresponding to energy terms). Once trained, the machine learning model 107 generates a second set of blueprint records that have a second set of scores associated with them. In some implementations, the computational protein modeling module 106 can be used to verify the second set of blueprint records and the second set of scores by computing a set of energy terms for the second set of blueprint records. The set of energy terms may be used to generate a set of ground-truth scores for the second set of blueprint records. A subset of blueprint records can be selected from the second set of blueprint records such that each blueprint record from the subset of blueprint records has a ground-truth score above a threshold. In some instances, the threshold can be a number predetermined by, for example, a user of the engineered polypeptide design device 101. In some other instances, the threshold can be a number dynamically determined based on the set of ground-truth scores.

The molecular dynamics simulation module 108 can be optionally used to verify the outputs of the machine learning model 107, after the machine learning model 107 is executed to generate the second set of blueprint records. The engineered polypeptide design device 101 may filter out a subset of the second blueprint records by generating engineered polypeptides based on the second set of blueprint records, and performing a dynamic structure comparison to the representation of the reference target structure using molecular dynamics (MD) simulations of the representation of the reference target structure and each of the structures of engineered polypeptides. For example, the molecular dynamics simulation module 108 may select a few (e.g., less than 10 hits) of the engineered polypeptides (that are based on the second set of blueprint records). In some instances, the MD simulations can be performed under boundary conditions, restraints, and/or equilibration. In some instances, the MD simulations can be performed under solution conditions including steps of model preparation, equilibration (e.g., temperatures of 100 K to 300 K), applying force field parameters and/or solvent model parameters to the representation of the reference target structure and each of the structures of engineered polypeptides. In some instances, the MD simulations can undergo restrained minimization (e.g., relieves structural clashes), restrained heating (e.g., restrained heating for 100 picoseconds and gradually increasing to an ambient temperature), relaxed restraints (e.g., relax restraints for 100 picoseconds and gradually removing backbone restraints), and/or the like.

In some implementations, the machine learning model 107 is an inductive machine learning model. Once trained, such machine learning model 107 may predict a score based on a blueprint record in a fraction of the time it normally would take by, for example, a numerical method to calculate a score for the blueprint (e.g., a computational protein modeling module, a density function theory based molecular dynamics energy simulator, and/or the like). Therefore, the machine learning model 107 can be used to estimate a set of scores of a set of blueprint records quickly to substantially improve an optimization speed (e.g., 50% faster, 2 times faster, 10 times faster, 100 times faster, 1000 times faster, 1,000,000 times faster, 1,000,000,000 times faster, and/or the like) of an optimization algorithm. In some implementations, the machine learning model 107 may generate a first set of scores for a first set of blueprint records. The processor 104 of the engineered polypeptide design device 101 may execute a code representing a set of instructions to select top performers of the first set of blueprint records (e.g., having top 10% of the first set of scores, e.g., having top 2% of the first set of scores, and/or the like). The processor 104 may further include code to verify scores of the top performers among the first set of blueprint records. In some variations, the top performers among the first set of blueprint records can be generated as output if their corresponding verified scores have a value larger than any of the first set of scores. In some variations the machine learning model 107 can be retrained based on a new data set including a second set of blueprint records and second set of scores that include the blueprint records and scores of the top performers.

The network 150 can be a digital telecommunication network of servers and/or compute devices. The servers and/or compute devices on the network can be connected via one or more wired or wireless communication networks (not shown) to share resources such as, for example, data storage or computing power. The wired or wireless communication networks between servers and/or compute devices of the network may include one or more communication channels, for example, a radio frequency (RF) communication channel(s), a fiber optic commination channel(s), and/or the like. The network can be, for example, the Internet, an intranet, a local area network (LAN), a wide area network (WAN), a metropolitan area network (MAN), a worldwide interoperability for microwave access network (WiMAX®), a virtual network, any other suitable communication system and/or a combination of such networks.

The backend service platform 160 may be a compute device (e.g., a server) operatively coupled to and/or within a digital communication network of servers and/or compute devices, such as for example, the Internet. In some variations, the backend service platform 160 may include and/or execute a cloud-based service such as, for example, a software as a service (SaaS), a platform as a service (PaaS), an infrastructure as a service (IaaS), and/or the like. In one example, the backend service platform 160 can provide data storage to store a large amount of data including protein structures, blueprint records, Rosetta energies, molecular dynamics energies, and/or the like. In another example, the backend service platform 160 can provide fast computing to execute a set of computational protein modeling, molecular dynamics simulations, training machine learning models, and/or the like.

In some variations, the procedure of the computational protein module 106 described herein can be executed in a backend service platform 160 that provides cloud computing services. In such variations, the engineered polypeptide design device 101 may be configured to send, using the communication interface 103, a signal to the backend service platform 160 to generate a set of blueprint records. The backend service platform 160 can execute a computational protein modeling process that generates the set of blueprint records. The backend service platform 160 can then transmit the set of blueprint records, via the network 150, to the engineered polypeptide design device 101.

In some variations, the engineered polypeptide design device 101 can transmit a file that includes the machine learning model 107 to a user compute device (not shown), remote from the engineered polypeptide design device 101. The user compute device can be configured to generate a set of blueprint records that meet design criteria (e.g., having a desired score). In some variations, the user compute device receives, from the engineered polypeptide design device 101, a reference target structure. The user compute device may generate a first set of blueprint records from a predetermined portion of the reference target structure such that each blueprint record includes target residue positions and scaffold residue positions. Each target residue position corresponds to one target residue from the set of target residues. The user compute device can further train the machine learning model based on a first set of blueprint records, or representations thereof, and a first set of scores. The user compute device may execute, after the training, the machine learning model to generate a second set of blueprint records having at least one desired score (e.g., meeting a certain design criteria). The second set of blueprint records may be received as input in computational protein modeling to generate engineered peptides based on the second set of blueprint records.

Figure 2:
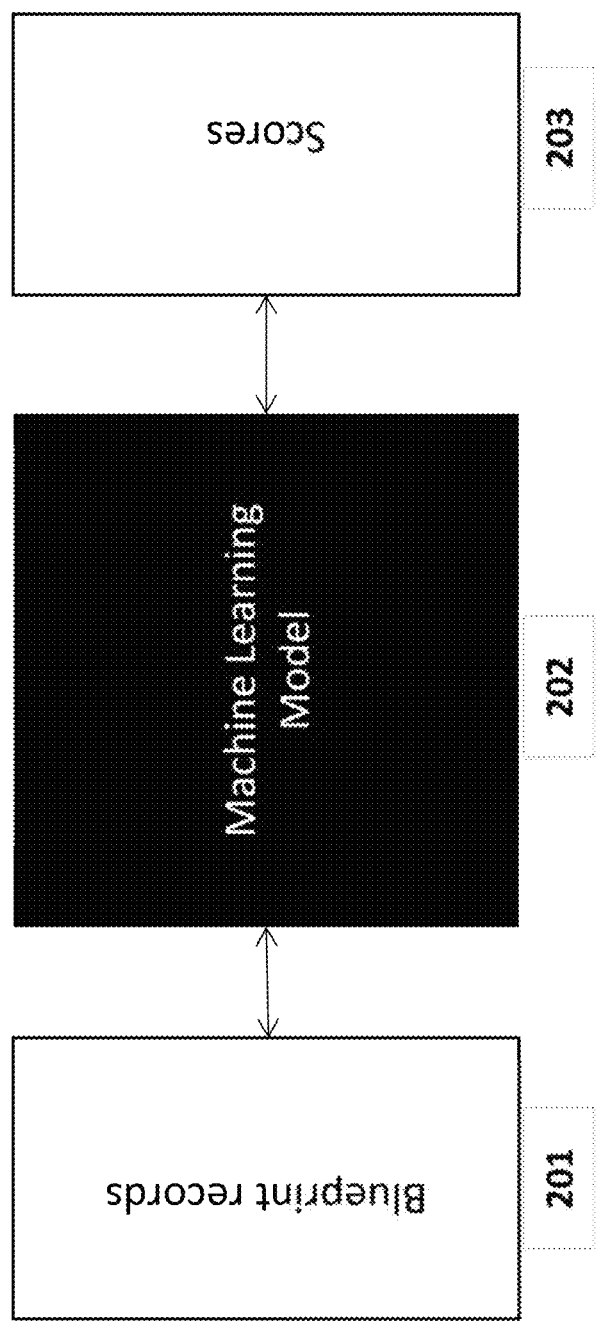
FIG. 2 is a schematic description of an exemplary machine learning model for engineered polypeptide design.

FIG. 2 is a schematic description of an exemplary machine learning model 202 (similar to the machine learning model 107 described and shown with respect to FIG. 1) for engineered polypeptide design. The machine learning model 202 may be a supervised machine learning model that correlates a design space of blueprint records with scores corresponding to energy terms of polypeptides constructed based on those blueprint records. The machine learning model may have a generative operation mode and/or an inductive operation mode.

In a generative operation mode, the machine learning model 202 is trained on a first set of blueprint records 201 and a first set of scores 203. Once trained, the machine learning model 202 generates a second set of blueprint records having a second set of scores that are statistically higher (e.g., having higher mean value) than the first set of scores. In an inductive operation mode, the machine learning model 202 is also trained on the first set of blueprint records 201 and the first set of scores 203. Once trained, the machine learning model 202 generates a second set of scores for a second set of blueprint records. The second set of scores are a set of predicted scores based on the historical training data (e.g. the first set of blueprint records and the first set of scores) and are generated substantially faster (e.g., 50% faster, 2 times faster, 10 times faster, 100 times faster, 1000 times faster, 1,000,000 times faster, 1,000,000,000 times faster, and/or the like) than numerically calculated scores and/or energy terms that use computational protein modeling (similar to the computational protein modeling module 106 as shown and described with respect to FIG. 1) or molecular dynamics simulation (similar to the molecular dynamics module 108 as shown and described with respect to FIG. 1).

FIG. 3 is a schematic description of an exemplary method of engineered polypeptide design 300. The method of engineered polypeptide design 300 can be performed, for example, by an engineered polypeptide design device (similar to engineered polypeptide design device 101 as shown and described with respect to FIG. 1). The method of engineered polypeptide design 300 optionally includes, at step 301, receiving a reference target structure for a reference target. The method of engineered polypeptide design 300 optionally includes, at step 302, generating the first set of blueprint records from a predetermined portion of the reference target structure, each blueprint record from the first set of blueprint records includes target residue positions and scaffold residue positions, each target residue position corresponding to one target residue from the set of target residues. In some instances, the target residues are nonconsecutive. In some instances, the target residues are non-ordered. The method of engineered polypeptide design 300 may include, at step 303, training a machine learning model (similar to the machine learning model 107 as shown and described with respect to FIG. 1) based on a first set of blueprint records, or representations thereof, and a first set of scores, each blueprint record from the first set of blueprint records associated with each score from the first set of scores. The representations may be generated based on the first set of blueprint records using a data preparation module (similar to the data preparation module as shown and described with respect to FIG. 1). The method of engineered polypeptide design 300 further includes, at step 304, executing, after the training, the machine learning model to generate a second set of blueprint records having at least one desired score (e.g., one score or a plurality of scores). In some configurations, the machine learning model includes a generative machine learning model and the at least one desired score is a preset value determined by a user of the engineered polypeptide design device. In some configurations, the machine learning model includes an inductive machine learning model that predicts a set of predicted scores for the second set of blueprint records. A subset of the second set of blueprint records can be selected such that each blueprint record from the subset of blueprint records have a score larger than the at least one desired score. In some configurations, the at least one desired score can be determined dynamically. For example, the at least one desired score can be determined to be the $90^{th}$ percentile of the set of predicted scores.

The method of engineered polypeptide design 300 optionally includes, at 305, determining whether to retrain the machine learning model by calculating a second set of scores (e.g., a ground-truth set of scores) by using a numerical method such as, for example, a Rosetta remodeler, an Ab initio molecular dynamics simulation, machine learning structure prediction such as AlphaFold or trRosetta, structural knowledgebase-backed protein folding, neural network protein folding, sequence-based recurrent or transformer network protein folding, generative adversarial network protein structure generation, Markov Chain Monte Carlo protein folding, and/or the like. The engineered polypeptide design device then compares the second set of scores with the set of predicted scores and based on deviation of the set of predicted scores from the second set of scores determines whether to retrain the machine learning model. The method of engineered polypeptide design 300 optionally includes, at 305, retraining, in response to the determining, the machine learning model based on (1) retraining blueprint records that include the second set of blueprint records and (2) retraining scores that include the set of predicted scores. In some configuration, the engineered polypeptide design device may concatenate the first set of blueprint records and the second set of blueprint records to generate the retrained blueprint records. The engineered polypeptide design device may further concatenate the first set of scores and the second set of scores to generate the retraining scores. In some configuration the retraining of the blueprint records only include the second set of blueprint records and the retraining scores only include the second set of scores.

Figure 4:
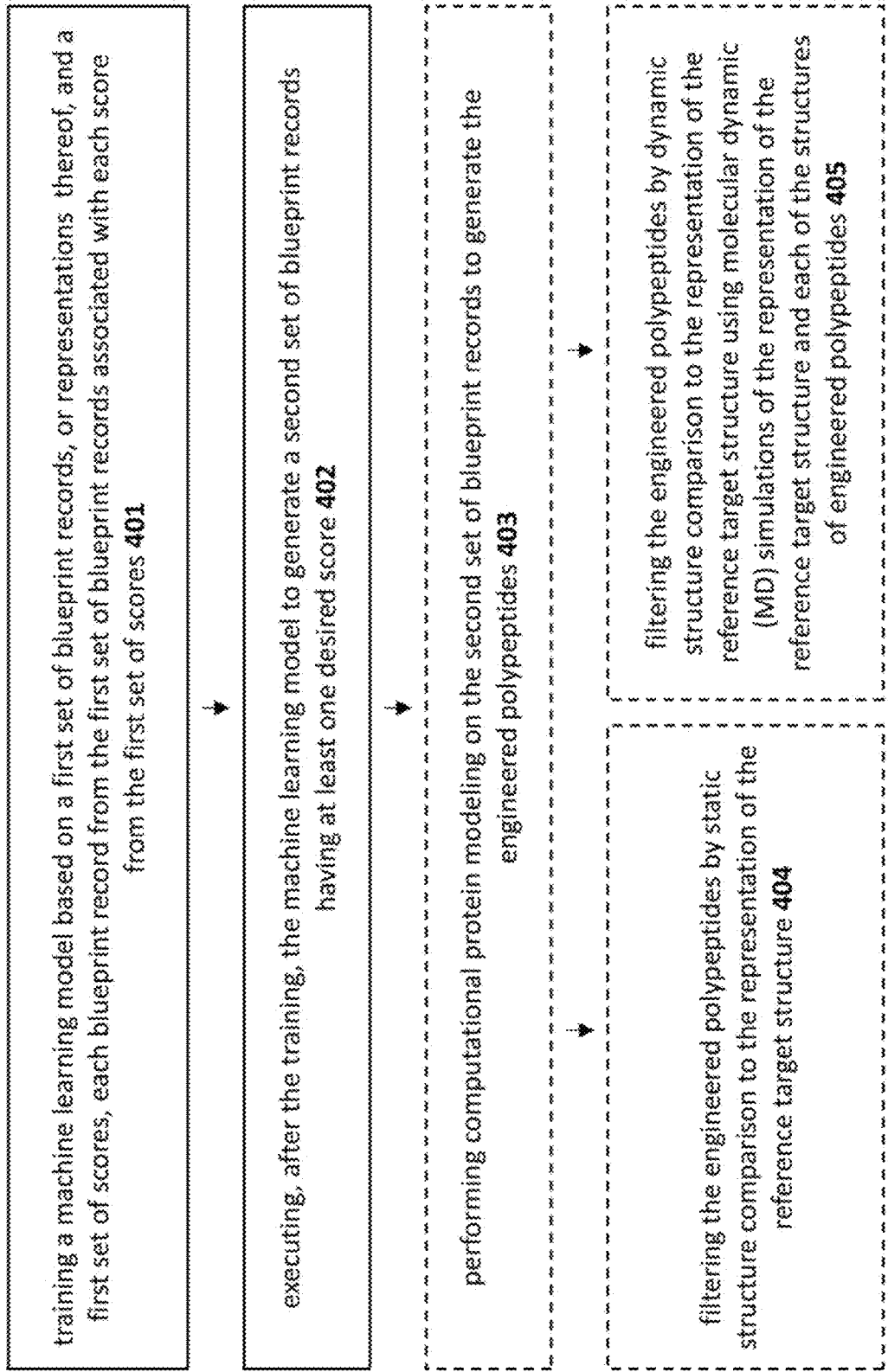
FIG. 4 is a schematic description of an exemplary method of engineered polypeptide design.

FIG. 4 is a schematic description of an exemplary method of engineered polypeptide design 400. The method of engineered polypeptide design 400 can be performed, for example, by an engineered polypeptide design device (similar to engineered polypeptide design device 101 as shown and described with respect to FIG. 1). The method of engineered polypeptide design 400 includes, at step 401, training a machine learning model (similar to the machine learning model 107 as shown and described with respect to FIG. 1) based on a first set of blueprint records, or representations thereof, and a first set of scores, each blueprint record from the first set of blueprint records associated with each score from the first set of scores. The representations may be generated based on the first set of blueprint records using a data preparation module (similar to the data preparation module as shown and describe with respect to FIG. 1). The method of engineered polypeptide design 400 further includes, at step 402, executing, after the training, the machine learning model to generate a second set of blueprint records having at least one desired score. The method of engineered polypeptide design 400 optionally includes, at step 403, performing computational protein modeling on the second set of blueprint records to generate the engineered polypeptides. In some configurations, the method of engineered polypeptide design 400 optionally includes, at step 404, filtering the engineered polypeptides by static structure comparison to the representation of the reference target structure. In some configurations, the method of engineered polypeptide design 400 optionally includes, at step 405, filtering the engineered polypeptides by dynamic structure comparison to the representation of the reference target structure using molecular dynamics (MD) simulations of the representation of the reference target structure and each of the structures of engineered polypeptides.

FIG. 5 is a schematic description of an exemplary method of preparing data for an engineered polypeptide design device. On the left is shown a ribbon diagram of the structure of a target protein. The predetermined portion is shown in darker color with the side chains of the amino-acid residues of the predetermined portion shown as stick diagrams. In this example, the predetermined portion is a portion of the target protein that is a desired target epitope for an antibody. By generating an engineered polypeptide to recapitulate this epitope, it is expected that antibodies that specifically bind this portion of the target protein can be obtained.

The right panel of FIG. 5 shows a diagram of a set of blueprints. Each circle denotes a residue position. The scaffold-residue positions are light gray and have no side chain shown. The target-residue positions are darker gray and the side chain of each is shown. The side chains are side chains of well known, naturally occurring amino acids. In some instances, the target-residues and/or scaffold-residues are unnatural amino acids. In this example, each target-residue position corresponds to exactly one residue of the predetermined portion of the reference target structure of the target protein. The set of blueprints shown are "ordered" in that in every diagram the target-residue positions are in the same order. The order of the target-residues is not necessarily in the same order as the residues in the target protein sequence. The first and last blueprint have continuous target-residue positions, whereas the other blueprints are discontinuous. At least one scaffold-residue position falls between the first and the last target-residue position. The letters N and C denote the amino (N) terminus and the carboxyl (C) terminus of a polypeptide matching the given blueprint.

The five blueprints shown in FIG. 5 are members of a vast set of possible blueprints, denoted by the ellipses between lines of the figure. For a blueprint with 35 positions (consistent with a 35-mer polypeptide), assuming the target residues are ordered, the total number of potential blueprints is given by the formula 35!÷(11!×(35−11)!)=0.42 trillion. Even utilizing the largest supercomputing services available, Rosetta remodeler calculations on all possible 35-mers would take years to lifetimes. Thus, direct computational modeling of each blueprint individually is computationally intractable using current computing devices and methods.

Figure 6:
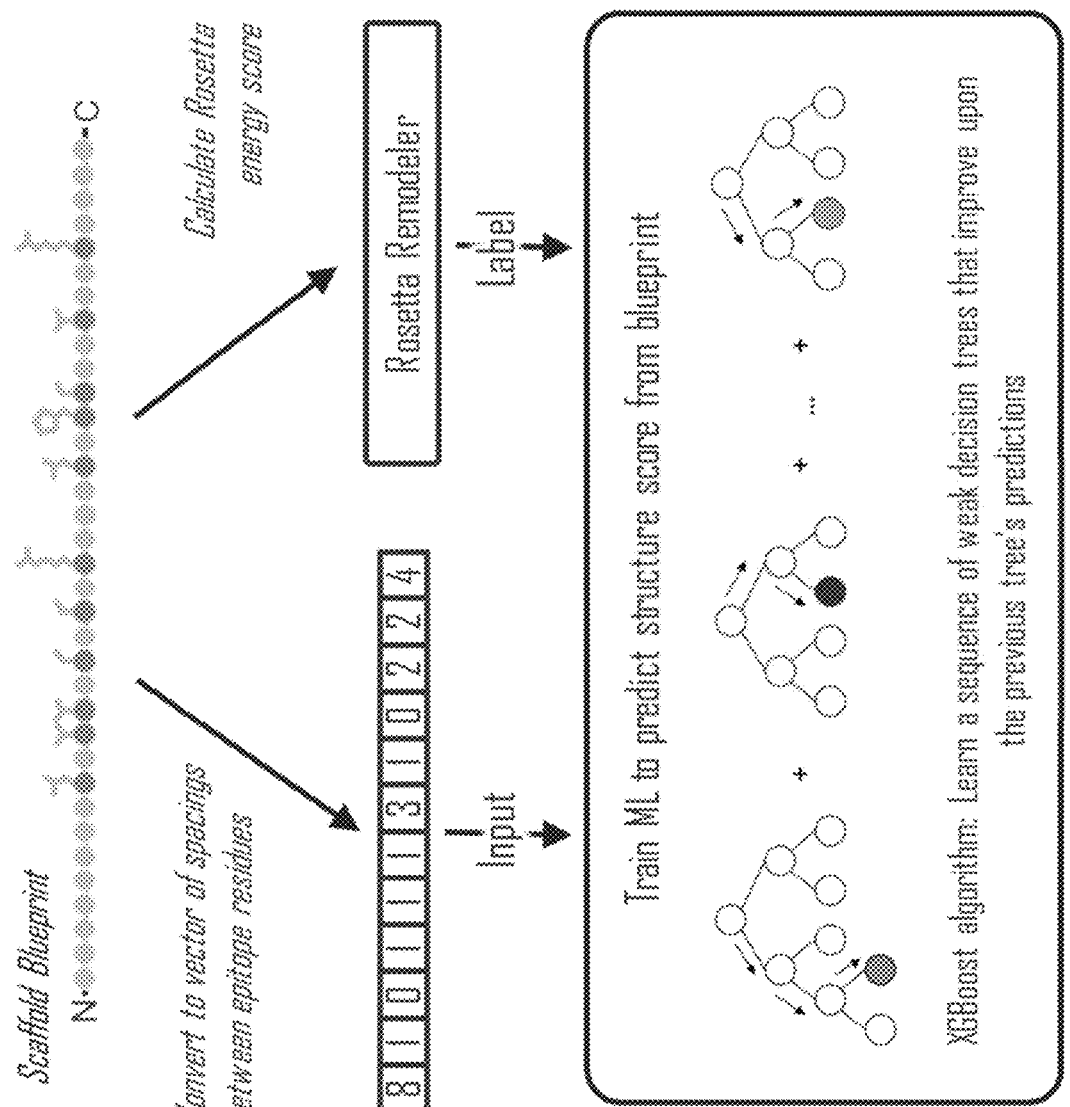
FIG. 6 is a schematic description of an exemplary method of engineered polypeptide design.

FIG. 6 is a schematic description of an exemplary method of engineered polypeptide design. The right-hand portion of schematic illustrates how the scaffold blueprint (e.g., converted to a blueprint record suitable for use as an input, not shown) can be fed into a computational protein modeling program (similar to the computational protein modeling module 106 as shown and described with respect to FIG. 1; including, but not limited to, a Rosetta remodeler) to generate a score for use as a label. The score will generally reflect the energy term used by the modeling program. In the case of Rosetta remodeler, this score includes both an energy term reflecting the folding of a designed polypeptide generated from the blueprint and a structure-constraint matching term reflecting structural similarity of the predicted structure of the designed polypeptide and the known structure of the predetermined portion of the reference target structure of the target protein. Other modeling programs and other scoring functions can be used.

The left-hand portion of the schematic illustrates converting the blueprint into a representation of the blueprint. The representation may be any representation suitable for use in a machine learning model (such as the machine learning model 107 as shown and described with respect to FIG. 1).

Here, the representation is a vector. More specifically, the vector is an ordered list of the number of intervening scaffold residues between target-residue positions. This representation may be used because the order of the target-residue positions is fixed in this representation, therefore the representation does not need to identify the amino acid identity of the target-residue positions. That information is implied. The order of the target-residue positions is not necessarily in the same order as in the target structure sequence. The first element of the vector, 8, indicates that there are eight scaffold-residue position before the first target-residue position. The second element of the vector, 1, indicates that after the first target-residue position there is one scaffold-residue position before the second target-residue position. Subsequent elements of 0, 1, 2, or 3 indicate no intervening scaffold-residue positions, one, two, or three intervening scaffold-residue positions. The last element of the vector, 4, indicates that the final four positions in the blueprint are scaffold-residue positions.

An advantage of this variation of the representation of the blueprint record is that other than the first and last elements the vector is frame-shift invariant. That is, the machine learning model has available information regarding the relative positions of the target residues independent of the position of the target residue within the blueprint. This permits design of similar structures with variable structured/unstructured regions at N- and C-terminus.

Figure 7:
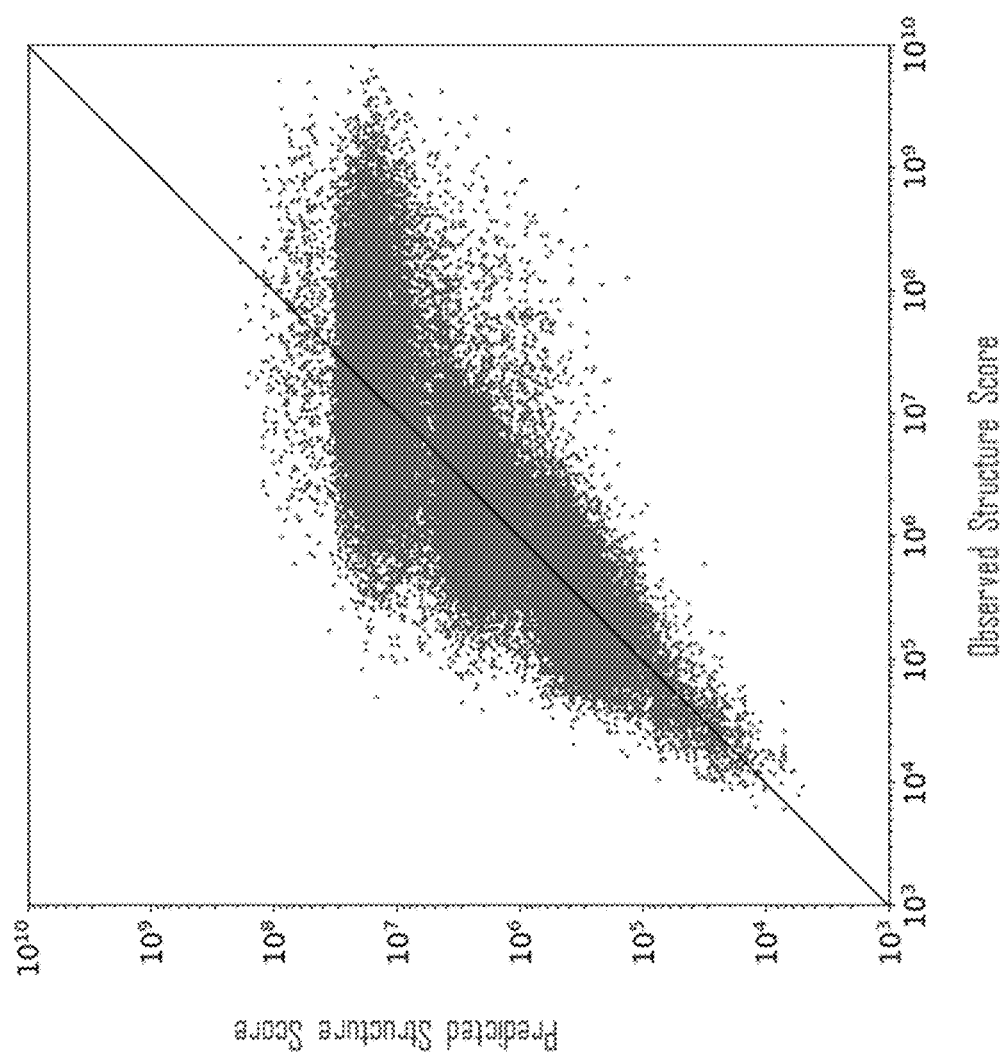
FIG. 7 is a schematic description of an exemplary performance of a machine learning model for engineered polypeptide design.

FIG. 7 is a schematic description of an exemplary performance of a machine learning model for engineered polypeptide design. The scatter plot illustrates how accurately a machine learning model (such as the machine learning model 107 as shown and described with respect to FIG. 1) can generate/predict a set of predicted scores for a set of blueprint records. Each dot in the scatter plot represents a blueprint record from the set of blueprint records. The horizontal axis represents ground-truth scores for the set of blueprint records that may be calculated by numerical methods such as, for example, a Rosetta remodeler, an Ab initio molecular dynamics simulation, and/or the like. The vertical axis represents predicted scores for the set of blueprint records that are generated/predicted by the machine learning model that operates substantially faster (e.g., 50% faster, 2 times faster, 10 times faster, 100 times faster, 1000 times faster, 1,000,000 times faster, 1,000,000,000 times faster, and/or the like) than the numerical methods. Ideally the predicted scores correspond to (e.g., are equal, approximate) the ground-truth scores. In an event that the predicted scores does not correspond to the ground-truth score, the machine learning model may be retrained by the set of blueprint records and the ground-truth score until newly generated predicted scores of a newly generated set of blueprint records correspond to ground-truth scores of the newly generated set of blueprint records. In general, the score may include both an energy term, such, for example, as the Rosetta Energy Function 2015 (REF15) and a structure-constraint matching term as described with respect to FIG. 6. The score can be defined such that a low score of the blueprint record reflect low molecular dynamics energy and higher stability of the blueprint record, as shown herein in FIG. 7. In some variations, a score can be defined such that a high score of a blueprint record generally reflect higher stability of a polypeptide that is constructed based on the blueprint record.

Figure 8:
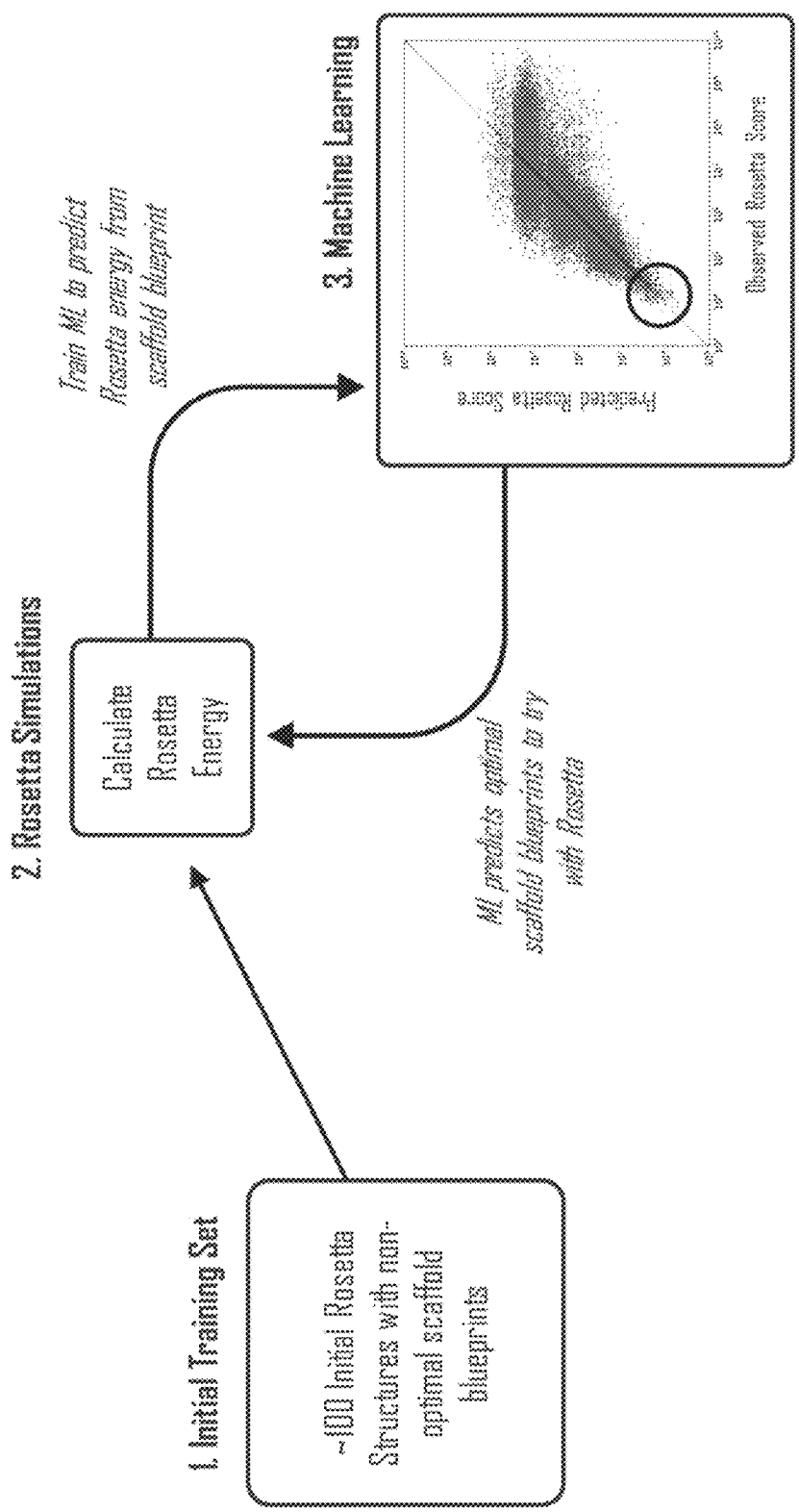
FIG. 8 is a schematic description of an exemplary method of using a machine learning model for engineered polypeptide design.
Figure 9:
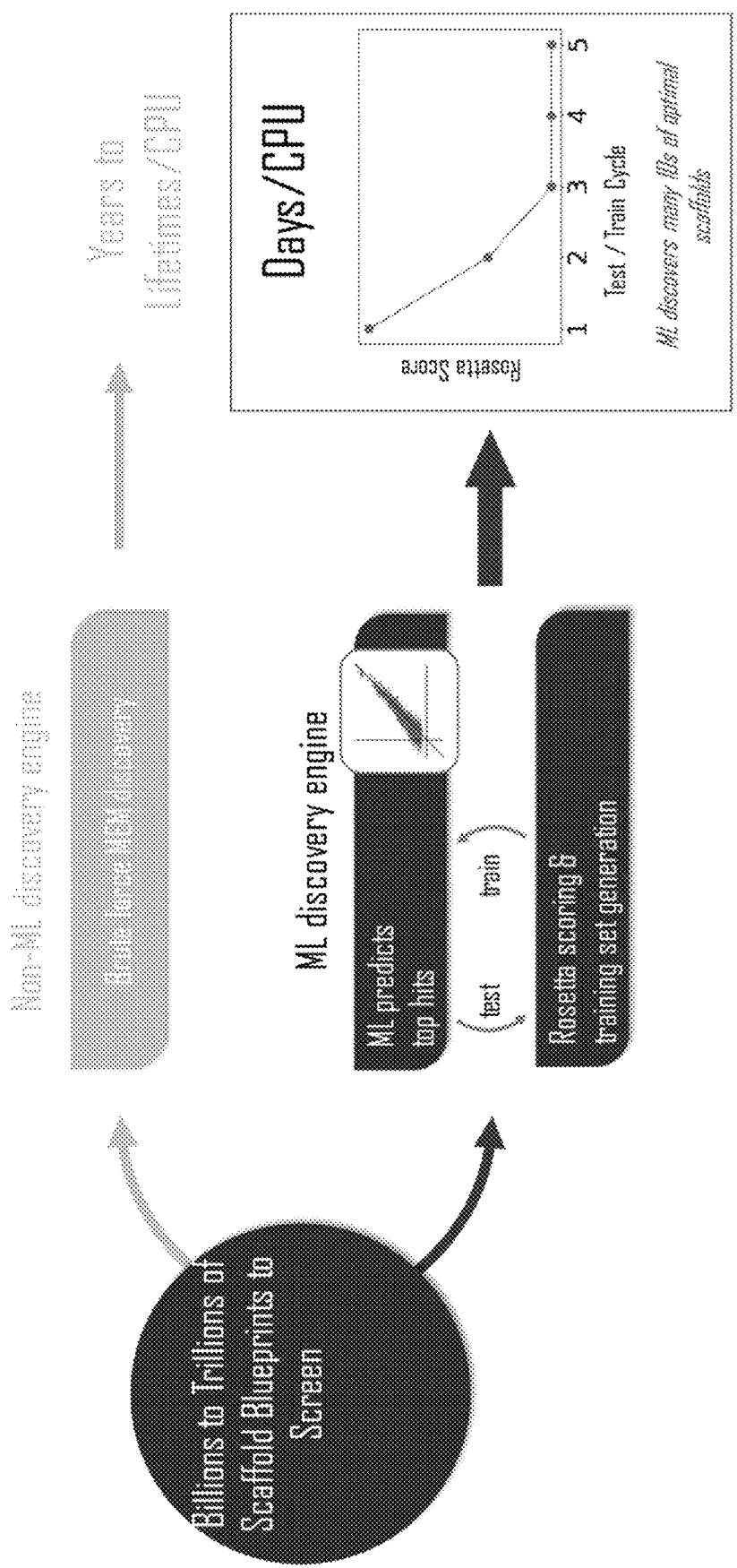
FIG. 9 is a schematic description of an exemplary performance of a machine learning model for engineered polypeptide design.
Figure 10A:
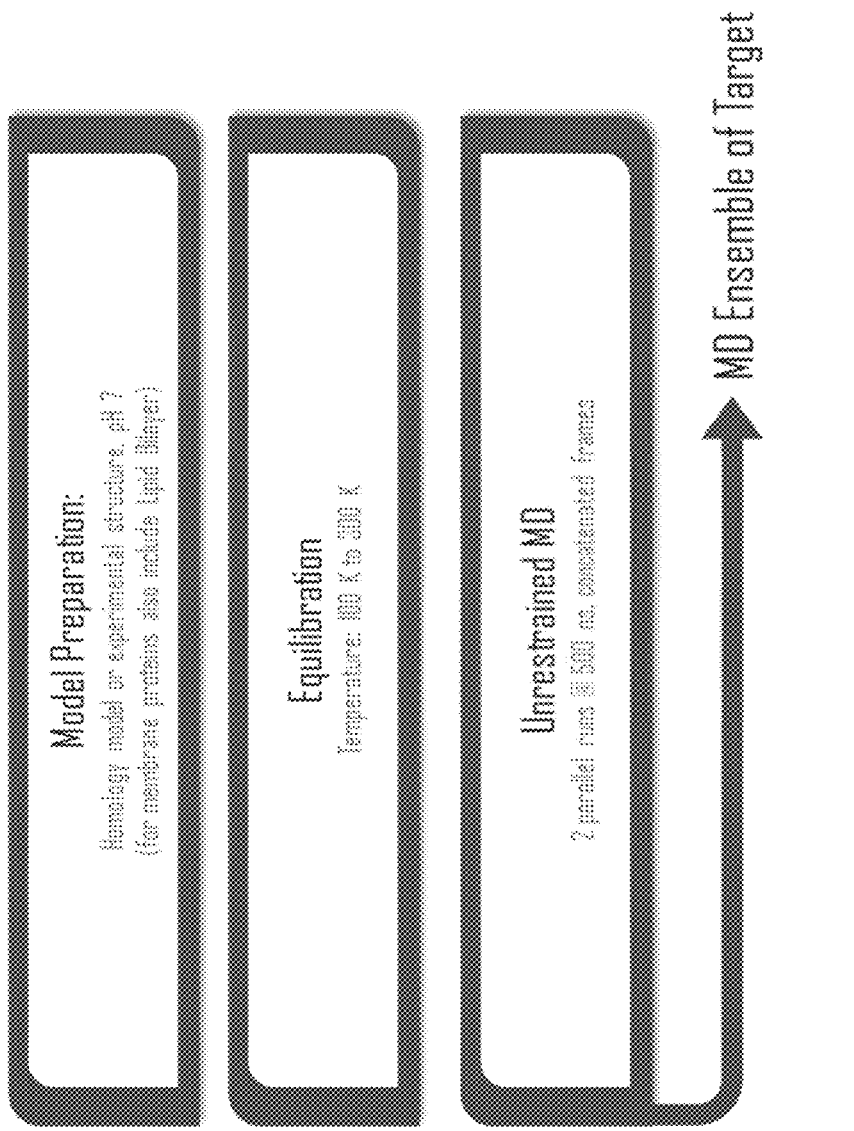
FIGS. 10A-D illustrate exemplary methods of performing molecular dynamics simulations to verify engineered polypeptides.
Figure 10B:
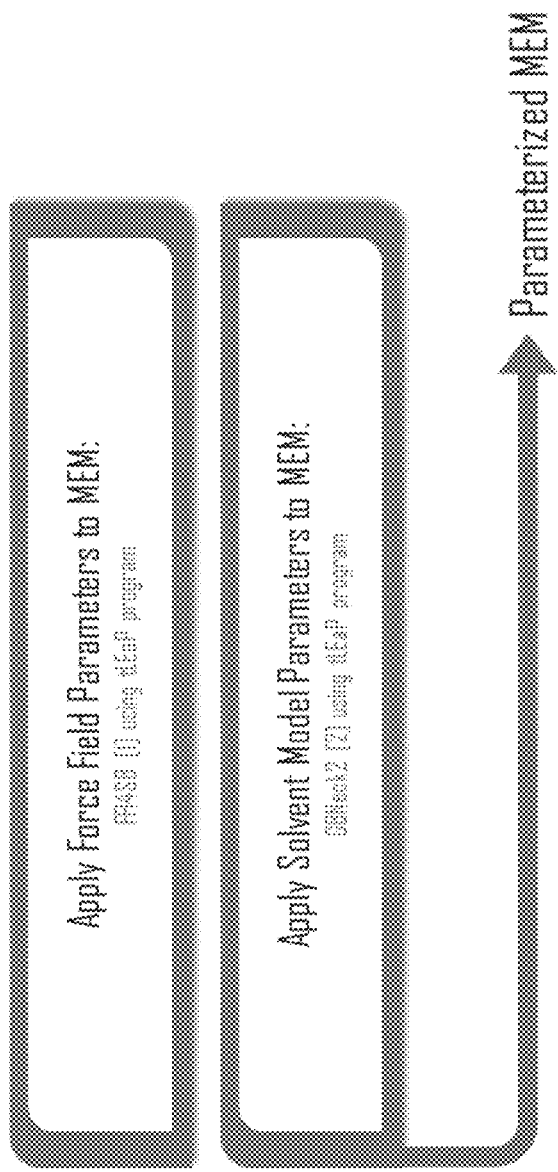
Figure 10C:
Figure 10D:
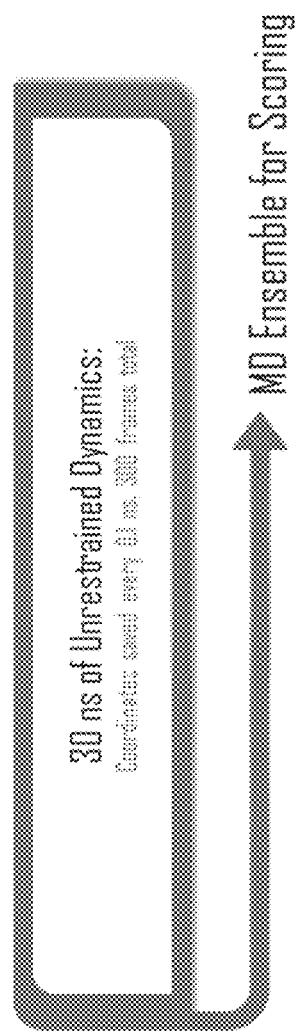

FIG. 8 is a schematic description of an exemplary method of using a machine learning model for engineered polypeptide design. As shown in FIG. 8 an initial set of data including a first set of blueprint records and a first set of scores (e.g., representing energy terms such as Rosetta energies or molecular dynamics energies) can be generated and be further prepared by a data preparation module (such as data preparation module 105 as shown and described with respect to FIG. 1). The machine learning model (similar to the machine learning model 107 as shown and described with respect to FIG. 1) can be trained based on the initial set of data. A second set of blueprint records can be given to the machine learning model as input to generate a second set of scores. The second set of blueprint records or a portion of the second set of blueprint records having scores above a predetermined value (e.g., a desired score) can be verified for ground-truth score. If the second set of scores correspond to the ground-truth scores accurately enough (e.g., having an accuracy of above 95%), the second set of blueprint records or the portion of the second set of blueprint records may be presented to a user. Otherwise, the second set of blueprint records or the portion of the second set of blueprint records may be used to retrain the machine learning model. In some instances, a third set of blueprint records, a fourth set of blueprint records, or a larger number of iterations of blueprint records may be generated in order to achieve blueprints with a desired score. In some instances, as many sets of blueprints as necessary to achieve a desired score are generated by iteratively retraining a machine learning model on new sets of blueprints and scores. An example code snippet illustrating a procedure for training and using the machine learning model for generating engineered polypeptide designs is as follows:

training_energies=Rosetta(training_scaffolds) ## Rosetta energies are calculated for the initial training set of scaffolds
while training_energies has not converged: ## Iterate until Rosetta energies stop improving
    train xgboost to predict training_energies from training_scaffolds ## Train XGBoost to predict Rosetta energy from the training set of scaffolds
    predicted_scaffolds=top predicted scaffolds from xgboost ## Predict optimal scaffolds with XGBoost
    new_energies=Rosetta(predicted_scaffolds) ## Rosetta energies are calculated for the predicted scaffolds
    add predicted_scaffolds to training_scaffolds ## Add predicted scaffolds to training set
    add new_energies to training_energies ## Add predicted scaffold energies to training set FIG. 9 is a schematic description of an exemplary performance of a machine learning model for engineered polypeptide design. As described with respect to FIG. 5, for an exemplary blueprint record with 35 positions (consistent with a 35-mer polypeptide), assuming the target residues are ordered, the total number of potential blueprints is given by the formula $35!\div(11!\times(35-11)!) = 0.42$ trillion. Thus, direct computational modeling of each blueprint individually using a brute force discover/optimization is computationally intractable using current computing devices and methods and might take years or many decades of time. In contrast, using data driven approaches such as the machine learning model, described herein, can reduce such discovery/optimization time (e.g., to weeks, days, hours, minutes, and/or the like).

FIGS. 10A-D illustrate exemplary methods of performing molecular dynamics simulations to verify engineered polypeptides. After a machine learning model (such as the machine learning model 107 as shown and described with respect to FIG. 1) is trained and executed to generate a set of generated blueprint records that are improved/optimized (e.g., meeting a design criteria, having a desired score, and/or the like), an engineered polypeptide design device (as described and shown with respect to FIG. 1) can verify the set of generated blueprint records.

The engineered polypeptide design device may perform computational protein modeling (e.g., using a computational design modeling module 106 as shown and described with respect to FIG. 1) on the set of generated blueprint records to generate engineered polypeptides. In some implementations, the engineered polypeptide design device may then filter out a subset of the engineered polypeptides by performing a static structure comparison to a representation of a reference target structure.

In some implementations, the engineered polypeptide design device may then filter out a subset of the engineered polypeptides by a dynamic structure comparison to the representation of the reference target structure using molecular dynamics (MD) simulations of the representation of the reference target structure and each of the structures of engineered polypeptides. For example, the engineered polypeptide design device may select a few (e.g., less than 10 hits) of the engineered polypeptides. In some instances, the MD simulations can determine dynamics of the representation of the reference target structure and each of the structures of engineered polypeptides under solution conditions including steps of model preparation, equilibration (e.g., temperatures of 100 K to 300 K), and unrestrained MD simulations. In some instances, the MD simulation can include applying force field parameters and solvent model parameters to the representation of the reference target structure and each of the structures of engineered polypeptides. In some instances, the MD simulations can undergo restrained minimization for 1000 cycles (e.g., relieves structural clashes), restrained heating (e.g., restrained heating for 100 picoseconds and gradually increasing to an ambient temperature), a relaxed restraints (e.g., relax restraints for 100 picoseconds and gradually removing backbone restraints).

FIG. 11 illustrates exemplary methods of performing molecular dynamics simulations to verify engineered polypeptides. In some implementations, additionally or alternatively to methods described with respect to FIG. 10, the MD simulations can be limited by time. For example, MD simulations can be executed for 30 ns of unrestrained dynamics. In some implementations, additionally or alternatively, the MD simulations can be limited by conformational information. For example, MD simulations can be executed to obtain 80% of conformational information observed with any time frame necessary to achieve such conformational information. In some implementations, a metric to determine simulation time that balances throughput and accuracy of the MD simulations can be calculated by a cosine similarity score of simulations of the representation of the reference target structure and each of the structures of engineered polypeptides.

Figure 12:
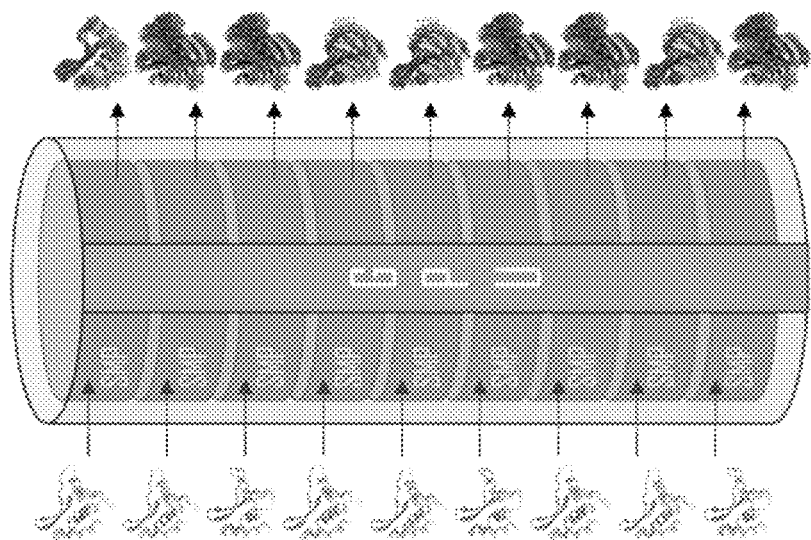
FIG. 12 is a schematic description of an exemplary method of parallelizing molecular dynamics simulations.

FIG. 12 is a schematic description of an exemplary method of performing molecular dynamics simulations in parallel. In some instances, engineered polypeptide design may involve performing many (e.g., 100s, 1000s, 10,000s, and/or the like) molecular dynamics simulations. In such instances, a processor of an engineered polypeptide design device (such as the processor 104 of the engineered polypeptide design device 101 as shown and describe with respect to FIG. 1) can include a graphical processing unit (GPU), an accelerated processing unit, and/or any other processing units that can perform computing in parallel. The GPU may include a set of symmetric multiprocessing units (SMPs). Thus, the GPU may be configured such as to process a number (e.g., 10s, 100s, and/or the like) of molecular dynamics simulation in parallel using the set of SMPs. In some variations, a multicore processing unit on a cloud computing platform (such as the backend service platform 160 shown and described with respect to FIG. 1) may be used to process the number of molecular dynamics simulations in parallel.

Figure 13:
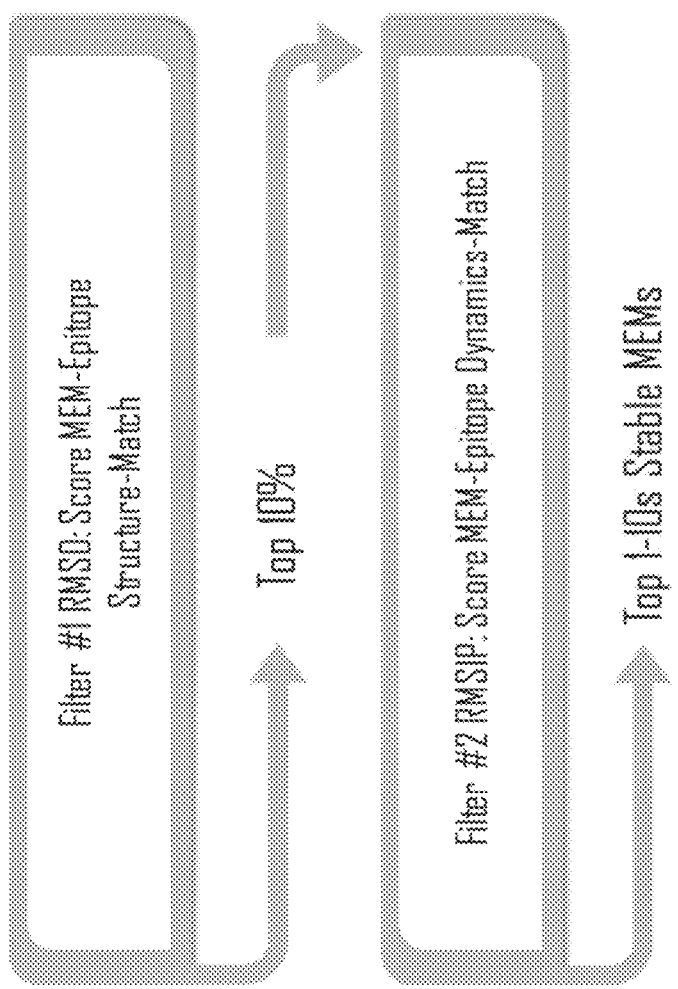
FIG. 13 is a schematic description of an exemplary method of verifying a machine learning model for engineered polypeptide design.

FIG. 13 is a schematic description of an exemplary method of verifying a machine learning model for engineered polypeptide design. In some implementations, a scoring method may be used on molecular dynamics (MD) simulation result of a representation of a reference target structure and MD simulation results of each of engineered polypeptides to evaluate each engineered polypeptide. The scoring method may involve using a root mean squared deviation (RMSD):

$$RMSD = \sqrt{\frac{\sum_{i=0}^{N}(X_i - Y_i)^2}{N}}$$

where N is the number of atoms, $X_i$ is the vector of reference positions of reference target structure and $Y_i$ is vector of positions of each engineered polypeptide. Alternatively, scoring MEM and epitope structure dynamic matching can be performed using a root mean squared inner product (RMSIP):

$$RMSIP = \sqrt{\frac{1}{N}\sum_{i=1}^{10}\sum_{j=1}^{10}(\varphi_i \cdot \psi_j)^2}$$

Where eigenvectors $\psi$ & $\varphi$ are eigenvectors of the reference target structure and eigenvectors of engineered polypeptides for N predetermined reference residues, respectively, sorted by corresponding eigenvalue—highest to lowest. Each of the eigenvectors $\psi$ & $\varphi$ represent lowest frequency modes of motions, in this case the top 10 eigenvectors, sorted by corresponding eigenvalues, are used. The eigenvectors of the reference target structure and the eigenvectors of engineered polypeptides can be calculated, for example, using principal component analysis (PCA).

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

ENUMERATED EMBODIMENTS

Embodiment I-1. A method, comprising:
training a machine learning model based on a first plurality of blueprint records, or representations thereof, and a first plurality of scores, each blueprint record from the first plurality of blueprint records associated with each score from the first plurality of scores; and executing, after the training, the machine learning model to generate a second plurality of blueprint records having at least one desired score, the second plurality of blueprint records configured to be received as input in computational protein modeling to generate engineered polypeptides based on the second plurality of blueprint records.

Embodiment I-2. The method of embodiment I-1, comprising:

receiving a representation of a reference target structure for a reference target; and generating the first plurality of blueprint records from a predetermined portion of the reference target structure, each blueprint record from the first plurality of blueprint records comprising target residue positions and scaffold residue positions, each target residue position corresponding to one target residue from the plurality of target residues.

Embodiment I-3. The method of embodiment I-1 or I-2, wherein in at least one blueprint record, the target residue positions are nonconsecutive.

Embodiment I-4. The method of any one of embodiments I-1 to I-3, wherein in at least one blueprint record, target residue positions in an order different from the order of the target residues positions in the reference target sequence.

Embodiment I-5. The method of any one of embodiments I-1 to I-4, comprising:

labeling the first plurality of blueprint records by, for each blueprint record from the first plurality of blueprint records:

performing computational protein modeling on that blueprint record to generate a polypeptide structure, calculating a score for the polypeptide structure, and associating the score with that blueprint record.

Embodiment I-6. The method of any one of embodiments I-1 to I-5, wherein the computational protein modeling is based on a de novo design without template matching to the reference target structure.

Embodiment I-7. The method of any one of embodiments I-1 to I-6, wherein each score from the first plurality of scores comprises an energy term and a structure-constraint matching term that is determined using one or more structural constraints extracted from the representation of the reference target structure.

Embodiment I-8. The method of any one of embodiments I-1 to I-7, comprising:

determining whether to retrain the machine learning model by calculating a second plurality of scores for the second plurality of blueprint records; and retraining, in response to the determining, the machine learning model based on (1) retraining blueprint records that include the second plurality of blueprint records and (2) retraining scores that include the second plurality of scores.

Embodiment I-9. The method of embodiment I-8, comprising:

concatenating, after the retraining the machine learning model, the first plurality of blueprint records and the second plurality of blueprint records to generate the retraining blueprint records and to generate the retraining scores, each blueprint record from the retraining blueprint records associated with a score from the retraining scores.

Embodiment I-10. The method of any one of embodiments I-1 to I-9, wherein the at least one desired score is a preset value.

Embodiment I-11. The method of any one of embodiments I-1 to I-9, wherein the at least one desired score is dynamically determined.

Embodiment I-12. The method of any one of embodiments I-1 to I-10, wherein the machine learning model is a supervised machine learning model.

Embodiment I-13. The method of embodiment I-12, wherein the supervised machine learning model includes an ensemble of decision trees, a boosted decision tree algorithm, an extreme gradient boosting (XGBoost) model, or a random forest.

Embodiment I-14. The method of embodiment I-12, wherein the supervised machine learning model includes a support vector machine (SVM), a feed-forward machine learning model, a recurrent neural network (RNN), a convolutional neural network (CNN), a graph neural network (GNN), or a transformer neural network.

Embodiment I-15. The method of any one of embodiments I-1 to I-14, wherein the machine learning model is an inductive machine learning model.

Embodiment I-16. The method of any one of embodiments I-1 to I-14, wherein the machine learning model is a generative machine learning model.

Embodiment I-17. The method of any one of embodiments I-1 to I-16, comprising performing computational protein modeling on the second plurality of blueprint records to generate the engineered polypeptides.

Embodiment I-18. The method of any one of embodiments I-1 to I-17, comprising filtering the engineered polypeptides by static structure comparison to the representation of the reference target structure.

Embodiment I-19. The method of any one of embodiments I-1 to I-18, comprising filtering the engineered polypeptides by dynamic structure comparison to the representation of the reference target structure using molecular dynamics (MD) simulations of the representation of the reference target structure and each of the structures of engineered polypeptides.

Embodiment I-20. The method of embodiment I-19, wherein the MD simulations are performed in parallel using symmetric multiprocessing (SMP).

Embodiment I-21. The method of any one of embodiments I-1 to I-20, wherein a number of blueprint records in the second plurality of blueprint records is less than a number of blueprint records in the first plurality of blueprint records.

Embodiment I-22. A non-transitory processor-readable medium storing code representing instructions to be executed by a processor, the code comprising code to cause the processor to:

train a machine learning model based on a first plurality of blueprint records, or representations thereof, and a first plurality of scores, each blueprint record from the first plurality of blueprint records associated with each score from the first plurality of scores; and execute, after the training, the machine learning model to generate a second plurality of blueprint records having at least one desired score, the second plurality of blueprint records configured to be received as input in computational protein modeling to generate engineered polypeptides based on the second plurality of blueprint records.

Embodiment I-23. The medium of embodiment I-22, comprising code to cause the processor to:

receive a representation of a reference target structure; and generating the first plurality of blueprint records from a predetermined portion of the reference target structure, each blueprint record from the first plurality of blueprint records comprising target residue positions and scaffold residue positions, each target residue position from the plurality of target residue positions corresponding to one target residue from the plurality of target residues.

Embodiment I-24. The medium of embodiments I-23, wherein in at least one blueprint record, the target residue positions are nonconsecutive.

Embodiment I-25. The medium of embodiment I-23 or I-24, wherein in at least one blueprint record, target residue positions in an order different from the order of the target residues positions in the reference target sequence.

Embodiment I-26. The medium of any one of embodiments I-23 to I-25, comprising code to cause the processor to:

label the first plurality of blueprint records by performing computational protein modeling on each blueprint record to generate a polypeptide structure, calculating a score for the polypeptide structure, and associating the score with the blueprint record.

Embodiment I-27. The medium of embodiment I-26, wherein the computational protein modeling is based on a de novo design without template matching to the reference target structure.

Embodiment I-28. The medium of embodiment I-26 or I-27, wherein each score comprises an energy term and a structure-constraint matching term that is determined using one or more structural constraints extracted from the representation of the reference target structure.

Embodiment I-29. The medium of any one of embodiments I-22 to I-28, comprising code to cause the processor to:

determining whether to retrain the machine learning model by calculating a second plurality of scores for the second plurality of blueprint records; and retraining, in response to the determining, the machine learning model based on (1) retraining blueprint records that include the second plurality of blueprint records and (2) retraining scores that include the second plurality of scores.

Embodiment I-30. The medium of embodiment I-29, comprising code to cause the processor to:

concatenating, after the retraining the machine learning model, the first plurality of blueprint records and the second plurality of blueprint records to generate the retraining blueprint records and to generate the retraining scores, each blueprint record from the retraining blueprint records associated with a score from the retraining scores.

Embodiment I-31. The medium of any one of embodiments I-22 to I-30, wherein the at least one desired score is a preset value.

Embodiment I-32. The medium of any one of embodiments I-22 to I-31, wherein the at least one desired score is dynamically determined.

Embodiment I-33. The medium of any one of embodiments I-22 to I-32, wherein the machine learning model is a supervised machine learning model Embodiment I-34. The medium of any one of embodiments I-22 to I-33, wherein the supervised machine learning model includes an ensemble of decision trees, a boosted decision tree algorithm, an extreme gradient boosting (XGBoost) model, or a random forest.

Embodiment I-35. The medium of embodiment I-33, wherein the supervised machine learning model includes a support vector machine (SVM), a feed-forward machine learning model, a recurrent neural network (RNN), a convolutional neural network (CNN), a graph neural network (GNN), or a transformer neural network.

Embodiment I-36. The medium of any one of embodiments I-22 to I-35, wherein the machine learning model is an inductive machine learning model.

Embodiment I-37. The medium of any one of embodiments I-22 to I-36, wherein the machine learning model is a generative machine learning model.

Embodiment I-38. The medium of any one of embodiments I-22 to I-37, comprising code to cause the processor to:

perform computational protein modeling on the second plurality of blueprint records to generate engineered polypeptides.

Embodiment I-39. The medium of embodiment I-38, comprising code to cause the processor to:

filter the engineered polypeptides by static structure comparison to the representation of the reference target structure.

Embodiment I-40. The medium of embodiment I-38 or I-39, comprising code to cause the processor to:

filter the engineered polypeptides by dynamic structure comparison to the representation of the reference target structure using molecular dynamics (MD) simulations of the representation of the reference target structure and each of the engineered polypeptides.

Embodiment I-41. The medium of embodiment I-40, wherein the MD simulations are performed in parallel using symmetric multiprocessing (SMP).

Embodiment I-42. The medium of any one of embodiments I-22 to I-41, wherein a number of blueprint records in the second plurality of blueprint records is less than a number of blueprint records in the first plurality of blueprint records.

Embodiment I-43. An apparatus of selecting an engineered polypeptide, comprising:

a first compute device having a processor and a memory storing instructions executable by the processor to:

receive, from a second compute device remote from the first compute device, a reference target structure;

generate a first plurality of blueprint records from a predetermined portion of the reference target structure, each blueprint record from the first plurality of blueprint records comprising target residue positions and scaffold residue positions, each target residue position corresponding to one target residue from the plurality of target residues.

train a machine learning model based on a first plurality of blueprint records, or representations thereof, and a first plurality of scores, each blueprint record from the first plurality of blueprint records associated with each score from the first plurality of scores; and execute, after the training, the machine learning model to generate a second plurality of blueprint records having at least one desired score, the second plurality of blueprint records configured to be received as input in computational protein modeling to generate engineered polypeptides based on the second plurality of blueprint records.

Embodiment I-44. The apparatus of embodiment I-43, comprising code to cause the processor to:

determining whether to retrain the machine learning model by calculating a second plurality of scores for the second plurality of blueprint records; and retraining, in response to the determining, the machine learning model based on (1) retraining blueprint records that include the second plurality of blueprint records and (2) retraining scores that include the second plurality of scores.

Embodiment I-45. The apparatus of embodiment I-43 or I-44, wherein the desired score is a preset value.

Embodiment I-46. The apparatus of any one of embodiments I-43 to I-45, wherein the desired score is dynamically determined.

Embodiment I-47. The apparatus of any one of embodiments I-43 to I-46, wherein the machine learning model is a supervised machine learning model Embodiment I-48. The apparatus of embodiment I-47, wherein the supervised machine learning model includes an ensemble of decision trees, a boosted decision tree algorithm, an extreme gradient boosting (XGBoost) model, or a random forest.

Embodiment I-49. The apparatus of embodiment I-47 or I-48, wherein the supervised machine learning model includes a support vector machine (SVM), a feed-forward machine learning model, a recurrent neural network (RNN), a convolutional neural network (CNN), a graph neural network (GNN), or a transformer neural network.

Embodiment I-50. The apparatus of any one of embodiments I-43 to I-49, wherein the machine learning model is an inductive machine learning model.

Embodiment I-51. The apparatus of any one of embodiments I-43 to I-50, wherein the machine learning model is a generative machine learning model.

Embodiment I-52. The apparatus of any one of embodiments I-43 to I-51, comprising code to cause the processor to:

perform computational protein modeling on the second plurality of blueprint records to generate engineered polypeptides.

Embodiment I-53. The apparatus of embodiment I-52, comprising code to cause the processor to:

filter the engineered polypeptides by static structure comparison to a representation of a reference target structure.

Embodiment I-54. The apparatus of embodiment I-52 or I-53, comprising code to cause the processor to:

filter the engineered polypeptides by dynamic structure comparison to a representation of a reference target structure using molecular dynamics (MD) simulations of the representation of the reference target structure and each of the engineered polypeptides.

Embodiment I-55. The apparatus of embodiment I-54, wherein the MD simulations are performed in parallel using symmetric multiprocessing (SMP).

Embodiment I-56. An engineered polypeptide design generated by the method of any one of embodiments I-1 to I-21, the medium of any one of embodiments I-22 to I-42, or the apparatus of any one of embodiments I-43 to I-55.

Embodiment I-57. An engineered peptide, wherein the engineered peptide has a molecular mass of between 1 kDa and 10 kDa and comprises up to 50 amino acids, and wherein the engineered peptide comprises:

a combination of spatially-associated topological constraints, wherein one or more of the constraints is a reference target-derived constraint; and wherein between 10% to 98% of the amino acids of the engineered peptide meet the one or more reference target-derived constraints, wherein the amino acids that meet the one or more reference target-derived constraints have less than 8.0 Å backbone root-mean-square deviation (RSMD) structural homology with the reference target.

Embodiment I-58. The engineered peptide of embodiment I-57, wherein the amino acids that meet the one or more reference target-derived constraints have between 10% and 90% sequence homology with the reference target.

Embodiment I-59. The engineered peptide of embodiments I-57 or I-58, wherein the combination comprises at least two reference target-derived constraints.

Embodiment I-60. The engineered peptide of any one of embodiments I-57 to I-59, wherein the combination comprises an energy term and a structure-constraint matching term that is determined using one or more structural constraints extracted from the representation of the reference target structure.

Embodiment I-61. The engineered peptide of any one of embodiments I-57 to I-60, wherein the one or more non-reference target-derived constraints describes a desired structural characteristic, dynamical characteristic, or any combinations thereof.

Embodiment I-62. The engineered peptide of any one of embodiments I-57 to I-61, wherein the reference target comprises one or more atoms associated with a biological response or biological function, and wherein the atomic fluctuations of the one or more atoms in the engineered peptide associated with a biological response or biological function overlap with the atomic fluctuations of the one or more atoms in the reference target associated with a biological response or biological function.

Embodiment I-63. The engineered peptide of embodiment I-62, wherein the overlap is a root mean square inner product (RMSIP) greater than 0.25.

Embodiment I-64. The engineered peptide of any one of embodiments I-62 or I-63, wherein the overlap has a root mean square inner product (RMSIP) greater than 0.75.

Embodiment I-65. A method of selecting an engineered peptide, comprising:

identifying one or more topological characteristics of a reference target;

designing spatially-associated constraints for each topological characteristic to produce a combination of spatially-associated topological constraints derived from the reference target;

comparing spatially-associated topological characteristics of candidate peptides with the combination of spatially-associated topological constraints derived from the reference target; and selecting a candidate peptide with spatially-associated topological characteristics that overlap with the combination of spatially-associated topological constraints derived from the reference target to produce the engineered peptide.

Embodiment I-66. The method of embodiment I-65, wherein one or more constraints is derived from per-residue energy and per-residue atomic distance.

Embodiment I-67. The method of any one of embodiments I-65 or I-66, wherein the characteristics of one or more candidate peptides are determined by computer simulation.

Embodiment I-68. The method of embodiment I-67, wherein the computer simulation comprises molecular dynamics simulations, Monte Carlo simulations, coarse-grained simulations, Gaussian network models, machine learning, or any combinations thereof.

Embodiment I-69. The method of any one of embodiments I-65 to I-68, wherein the amino acids meeting the one or more reference target-derived constraints have between 10% and 90% sequence homology with the reference target.

Embodiment I-70. The method of any one of embodiments I-65 to I-69, wherein the one or more non-reference target-derived constraints describes a desired structural characteristic and/or dynamical characteristic.

The invention claimed is:

1. A method for designing engineered polypeptides using a machine learning model, comprising:
   (a) receiving a representation of a reference target structure for a reference target;
   (b) generating a training set of blueprint records from a predetermined portion of the reference target structure, wherein each blueprint record comprises target residue positions and scaffold residue positions, each target residue position corresponding to one target residue from the plurality of target residues;
   (c) labeling each blueprint record of the training set of blueprint records with a score by, for each blueprint record of the training set:
      (i) performing computational protein modeling on that blueprint record to generate a polypeptide structure,
      (ii) calculating a score for the polypeptide structure, and
      (iii) associating the score with that blueprint record;
   (d) training a machine learning model based on the labeled training set; and
   (e) applying the trained machine learning model to a set of desired scores to generate an output set of blueprint records with the desired scores.

2. The method of claim 1, wherein in at least one blueprint record, the target residue positions are nonconsecutive.

3. The method of claim 1, wherein in at least one blueprint record, the target residue positions are in an order different from the order of target residues positions in the reference target structure.

4. The method of claim 1, wherein the computational protein modeling is based on a de novo design without template matching to the reference target structure.

5. The method of claim 1, wherein each score in the labeling step comprises at least an energy term and a structure-constraint matching term that is determined using one or more structural constraints extracted from the representation of the reference target structure.

6. The method of claim 1, wherein the set of desired scores is dynamically determined.

7. The method of claim 1, wherein the machine learning model is a supervised machine learning model.

8. The method of claim 1, comprising performing computational protein modeling on the output set of blueprint records to generate predicted structures of engineered polypeptides.

9. The method of claim 8, comprising:
   filtering the predicted structures of the engineered polypeptides by static structure comparison to the representation of the reference target structure.

10. The method of claim 1, further comprising generating a polypeptide sequence from a blueprint record of the output set of blueprint records by computational protein modeling.

11. The method of claim 1, further comprising producing a polypeptide having a polypeptide sequence generated from a blueprint record of the output set of blueprint records by computational protein modeling.

12. A non-transitory processor-readable medium storing code representing instructions to be executed by a processor for designing engineered polypeptides using a machine learning model, the code comprising code to cause the processor to:
   (a) receive a representation of a reference target structure for a reference target;
   (b) generate a training set of blueprint records from a predetermined portion of the reference target structure, wherein each blueprint record comprises target residue positions and scaffold residue positions, each target residue position corresponding to one target residue from the plurality of target residues;
   (c) label each blueprint record of the training set of blueprint records with a score by, for each blueprint record of the training set:
      (i) performing computational protein modeling on that blueprint record to generate a polypeptide structure,
      (ii) calculating a score for the polypeptide structure, and
      (iii) associating the score with that blueprint record;
   (d) train a machine learning model based on the labeled training set; and
   (e) apply the trained machine learning model to a set of desired scores to generate an output set of blueprint records with the desired scores.

13. The non-transitory processor-readable medium of claim 12, wherein the set of desired scores is dynamically determined.

14. The non-transitory processor-readable medium of claim 12, wherein the machine learning model is a supervised machine learning model.

15. The non-transitory processor-readable medium of claim 12, comprising code to cause the processor to:
   perform computational protein modeling on the output set of blueprint records to generate predicted structures of engineered polypeptides.

16. The non-transitory processor-readable medium of claim 15, comprising code to cause the processor to:
   filter the predicted structures of the engineered polypeptides by static structure comparison to a representation of a reference target structure.

17. The non-transitory processor-readable medium of claim 12, comprising code to cause the processor to
   generate a polypeptide sequence from a blueprint record of the output set of blueprint records by computational protein modeling.

18. The non-transitory processor-readable medium of claim 12, comprising code to cause the processor to
   produce a polypeptide having a polypeptide sequence generated from a blueprint record of the output set of blueprint records by computational protein modeling.

* * * * *